United States Patent [19]

Kleemann et al.

[11] Patent Number: 5,707,932
[45] Date of Patent: Jan. 13, 1998

[54] HERBICIDAL PICOLINAMIDE DERIVATIVES

[75] Inventors: Axel Kleemann, Hanau; Robert John Griffith Searle, Schwabenheim, both of Germany

[73] Assignee: American Cyanamid Company, Parsippany, N.J.

[21] Appl. No.: 325,173

[22] PCT Filed: Oct. 21, 1993

[86] PCT No.: PCT/EP93/02925

§ 371 Date: Aug. 4, 1995

§ 102(e) Date: Aug. 4, 1995

[87] PCT Pub. No.: WO94/08991

PCT Pub. Date: Apr. 28, 1994

[30] Foreign Application Priority Data

Oct. 22, 1992 [EP] European Pat. Off. ............. 92118039

[51] Int. Cl.⁶ ...................... A01N 43/56; C07D 401/02
[52] U.S. Cl. ............................. 504/253; 546/276.1
[58] Field of Search ................... 546/276.1; 504/253

[56] References Cited

U.S. PATENT DOCUMENTS

| 4,251,263 | 2/1981 | Gutman | 546/291 |
| 4,772,309 | 9/1988 | Stetter et al. | 548/124 |

FOREIGN PATENT DOCUMENTS

0488474 A1  6/1992  European Pat. Off.

*Primary Examiner*—Jane Fan
*Attorney, Agent, or Firm*—Gregory M. Hill

[57] ABSTRACT

Herbicidal picolinamide derivatives are provided having the formula I

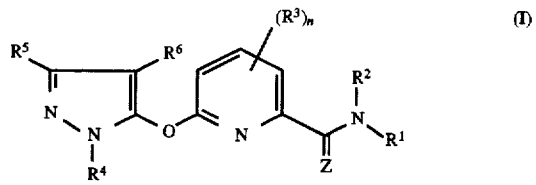

which Z represents an oxygen or sulphur atom, $R^1$ and $R^2$ each independently represents a hydrogen atom or an optionally substituted alkyl, alkenyl, alkynyl, cycloalkyl, cycloalkylalkyl, aryl, aralkyl, alkaryl, hydroxy, alkoxy, alkenyloxy, alkynyloxy, alkylcarbonyl, amino, mono- or di-alkylamino, alkoxycarbonylamino, arylamino, arylalkylamino or dialkylcarbamoyl group, or together represent an alkylene chain which is optionally interrupted by an oxygen or sulphur atom or by a group —NR— in which R represents a hydrogen atom or an alkyl group, $R^3$ independently represents a halogen atom or an alkyl or haloalkyl group, $R^4$, $R^5$ and $R^6$ each independently represents a hydrogen or halogen atom, an optionally substituted alkyl, alkenyl, alkynyl, cycloalkyl, cycloalkylalkyl, aryl, aralkyl, alkaryl, alkoxy, amino, mono- or di-alkylamino, alkoxycarbonylamino, arylamino, dialkylcarbamoyl, acyl or acylamido group or a cyano group, with the proviso that $R^5$ and $R^6$ do not represent an acyl, acylamido or cyano group, and n represents 0, 1, 2 or 3.

10 Claims, No Drawings

HERBICIDAL PICOLINAMIDE DERIVATIVES

This is a 371 of PCT/EP93/02925 filed Oct. 21, 1993 now WO 94/08991 Apr. 28, 1994.

The invention relates to certain pyrazolyloxypicolinamide derivatives, process for their preparation, compositions containing such compounds and their use as herbicides to combat undesired plant growth.

The herbicidal activity of 2-phenoxy-3-pyridine carboxamide compounds is well known. In 1981 and 1982 three U.S. patent specifications were published. U.S. Pat. Nos. 4,251,263, 4,270,946 and 4,327,218, directed to A. D. Gutman's work on 2-phenoxynitcotinamide herbicides. His later review articles, Chapter 5 of "Synthesis and Chemistry of Agrochemicals" (1987) published by the American Chemical Society, shows that his investigations started with 2-phenoxynicotinic acids (which were found to be inactive) progressed to N-alkyl amide derivatives (found to have weak herbicidal activity), and then concentrated on N-phenyl and N-benzyl amides as the most active of the compound type. Indeed, diflufenican [N-(2,4-difluorophenyl)-2-(3-trifluoromethylphenoxy)-3-pyridine carboxamide] was subsequently developed, by a different research group, as a commercial herbicide for use against broad-leaved weeds in winter cereals, such as winter wheat and barley.

U.S. Pat. No. 4,251,263 is concerned with the N-alkyl amides of Gutman, and related N-alkenyl and N-alkynyl amides. The compound documented as being the most active of the aliphatic amides prepared and tested is N-(1,1-dimethylprop-2-ynyl)-2-(3-trifluoromethylphenoxy)-3-pyridine carboxamide, which gives 85% control pre-emergence and only 57% control post-emergence on specified narrow- and broad-leaved species.

EP-A-0488474 discloses herbicidal 2-phenoxy-6-pyridine carboxamide compounds of the general formula:

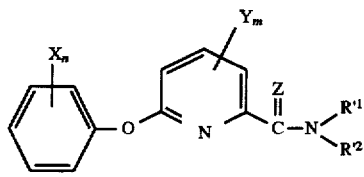

wherein n is an integer from 1 to 5 and the or each X independently represents a hydrogen or halogen atom, an alkyl group optionally substituted by one or more of the same or different substituents selected from halogen atoms and cyano, hydroxy and alkoxy groups, or a cyano, nitro, alkenyloxy, alkynyloxy, alkylthio, haloalkylthio or alkylnylthio group;

m is 0 or an integer from 1 to 3 and the or each Y independently represents a halogen atom or an alkyl or haloalkyl group;

Z represents an oxygen atom or a sulphur atom; and

R'¹ and R'² each, independently, represents a hydrogen atom, an alkyl group optionally substituted by one or more of the same or different substituents selected from halogen atoms or hydroxy, cyano, alkoxy, alkylthio, alkoxycarbonyl, or mono- or di-alkylamino groups, an alkenyl, alkynyl, cycloalkyl, or optionally substituted cycloalkylalkyl group, or a hydroxy, alkoxy, alkenyloxy, alkynyloxy, alkoxycarbonyl, amino, mono- or di-alkylamino, alkoxycarbonylamino group, an arylamino group optionally substituted by a halogen atom, or a dialkylcarbamoyl group; or R'¹ and R'² together represent an alkylene chain which is optionally interrupted by an oxygen or sulphur atom or by a group —NR— in which R represents a hydrogen atom or an alkyl group.

It has now been found that certain new pyrazolyloxypicolinamide compounds show excellent herbicidal activity against representative narrow- and broad-leaved test species in pre- and/or post-emergence application, certain examples exhibiting 90 to 100% effectiveness against test species both pre- and post-emergence.

The present invention therefore relates to compounds of the general formula I

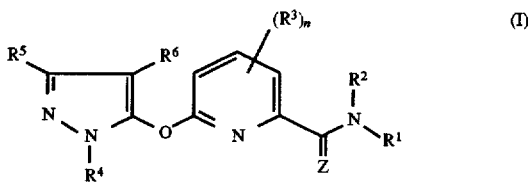

in which

Z represents an oxygen or sulphur atom, $R^1$ and $R^2$ each independently represent a hydrogen atom or an optionally substituted alkyl, alkenyl, alkynyl, cycloalkyl, cycloalkylalkyl, aryl, aralkyl or alkaryl group or one but not both of $R^1$ and $R^2$ may additionally represent a hydroxy group or an optionally substituted alkoxy, alkenyloxy, alkynyloxy, alkylcarbonyl, amino, mono- or di-alkylamino, alkoxycarbonylamino, arylamino, arylalkylamino or dialkylcarbamoyl group, or together $R^1$ and $R^2$ represent an alkylene chain which is optionally interrupted by an oxygen or sulphur atom or by a group —NH— in which R represents a hydrogen atom or an alkyl group, $R^3$ or each $R^3$ independently represents halogen atom or an alkyl, alkoxy, alkylthio, dialkylamino or haloalkyl group, $R^4$ represents a hydrogen or halogen atom or an optionally substituted alkyl, alkenyl, alkynyl, cycloalkyl, cycloalkylalkyl, aryl, aralkyl, alkaryl, alkoxy, dialkylcarbamoyl, acyl or cyano group, and $R^5$ and $R^6$ each independently represents a hydrogen or halogen atom, an optionally substituted alkyl, alkenyl, alkynyl, cycloalkyl, cycloalkylalkyl, aryl, aralkyl, alkaryl, alkoxy, amino, mono- or di-alkylamino, alkoxycarbonylamino, arylamino, dialkylcarbamoyl group, and n represents 0, 1, 2 or 3.

The invention especially relates to compounds of the general formula I in which any alkyl, alkenyl, alkynyl part of any of the substituents $R^1$ to $R^6$ contains up to 12 carbon atoms, preferably up to 10 carbon atoms, any cycloalkyl part of any of the substituents $R^1$ to $R^6$ contains from 3 to 10 carbon atoms, preferably from 3 to 8 carbon atoms, any alkylene chain, optionally interrupted by an oxygen or sulphur atom or by a group —NR— in which R represents a hydrogen atom or an alkyl group, contains from 2 to 8 chain members, preferably from 2 to 6 chain members and any aryl part of any of the substituents $R^1$ to $R^6$ contains 6, 10 or 14 carbon atoms, preferably 6 or 10 carbon atoms, and in which said optional substituents are selected from the group consisting of halogen atoms or nitro, cyano, alkyl, preferably $C_{1-6}$ alkyl, haloalkyl, preferably $C_{1-6}$ haloalkyl, alkoxy, preferably $C_{1-6}$ alkoxy, haloalkoxy, preferably $C_{1-6}$ haloalkoxy, optionally substituted amino, formyl, alkoxycarbonyl, preferably $C_{1-6}$ alkoxycarbonyl, carboxyl, phenyl or halo- or dihalo-phenyl groups. Optionally substituted amino groups include amino groups substituted by one or two groups selected from alkyl, aryl, cycloalkyl, cycloalkylalkyl, arylalkyl and aralkyl groups, in particular alkylamino, dialkylamino, arylmethylamino and arylamino. Any acyl group includes formyl, optionally substituted alkyl carbonyl and optionally substituted aryl carbonyl groups. Any alkyl, alkenyl or alkynyl group may be linear or branched. Preferred alkyl substituents are at least methyl, ethyl, propyl, butyl and pentyl. A preferred aryl substituent is a phenyl group. A halogen atom suitably denotes a fluorine, chlorine or bromine atom.

The invention especially relates to compounds of the general formula I in which Z represents an oxygen atom.

The invention especially relates to compounds of the general formula I in which $R^1$ and $R^2$ each independently represents a hydrogen atom or a $C_{1-8}$ alkyl, $C_{1-8}$ alkenyl, $C_{1-8}$ alkynyl, $C_{3-6}$ cycloalkyl, ($C_{3-6}$ cycloalkyl) $C_{1-8}$ alkyl, $C_{1-6}$ alkoxy, phenyl, naphthyl, phen-$C_{1-6}$ alkyl, $C_{1-8}$ alkylamino, $C_{1-6}$ dialkylamino or phenylamino group, each group optionally substituted by one or more halogen atoms or $C_{1-4}$ alkyl, $C_{1-4}$ haloalkyl, $C_{1-4}$ alkoxy, $C_{1-4}$ alkylamino, $C_{1-4}$ dialkylamino, cyano or phenyl amino groups, or together represent a $C_{2-6}$ alkylene chain, with the proviso that only one of $R^1$ and $R^2$ represents an optionally substituted $C_{1-6}$ alkoxy, $C_{1-8}$ alkylamino, $C_{1-6}$ dialkylamino or phenylamino group. Preferably $R^1$ represents a $C_{1-6}$ alkyl, $C_{1-4}$ alkenyl, $C_{1-6}$ alkynyl, $C_{3-6}$ cycloalkyl, phenyl, benzyl, $C_{1-4}$ alkylamino, $C_{1-4}$ dialkylamino or phenylamino group, each group optionally substituted by one or more fluorine, chlorine or bromine atoms, especially fluorine or chlorine atoms, or a cyano, $C_{1-4}$ alkyl or $C_{1-4}$ alkoxy group, and $R^2$ represents a hydrogen atom or a $C_{1-4}$ alkyl group.

The invention especially relates to compounds of the general formula I in which $R^3$ represents a methyl, methoxy, methylthio or dimethylamino group, preferably methyl. The substituent(s) $R^3$ may be at any free position or combination of positions on the pyridyl ring. A preferred position is the 4-position.

The invention further especially relates to compounds of the general formula I in which $R^4$, $R^5$ and $R^6$ each independently represents a hydrogen atom, a cyano group or a $C_{1-4}$ alkyl, $C_{3-6}$ cycloalkyl, $C_{1-4}$ acyl, $C_{1-4}$ alkenyl, phenyl or naphthyl group, each group optionally substituted by one or more halogen atoms, especially fluorine atoms, or $C_{1-4}$ alkyl, $C_{1-4}$ haloalkyl, $C_{1-4}$ alkoxy, $C_{1-4}$ alkylamino, $C_{1-4}$ dialkylamino or aryl amino groups, with the proviso that $R^4$ does not represent a cyano group or an optionally substituted $C_{1-4}$ acyl group.

The invention also especially relates to compounds of the general formula I in which $R^4$ represents a hydrogen atom, a $C_{1-4}$ alkyl group or a phenyl group optionally substituted by a halogen atom, $R^5$ represents a hydrogen atom or a $C_{1-6}$ alkyl or phenyl group, each group optionally substituted by one or more halogen atoms, especially fluorine atoms, or represents a $C_{3-6}$ cycloalkyl group and $R^6$ represents a hydrogen atom or a $C_{1-4}$ alkyl group, optionally substituted by one or more halogen atoms.

The invention especially relates to compounds of the general formula I in which n represents 0 or 1.

A particularly preferred sub-group of compounds of the general formula I is that in which $R^1$ represents a methyl, ethyl, propyl, allyl, butyl, pentyl, including neopentyl, methylallyl, propynyl, dimethylpropynyl, methoxyethyl, cyanomethyl, cyclopropyl, cyclobutyl, cyclopentyl, chloroethyl, trifluoroethyl, cyclopropylmethyl, dichlorocyclopropylmethyl, t-butoxy, phenyl, fluorophenyl, difluorophenyl, trifluoroethylamino, butylamino, dimethylamino, phenylamino or fluorophenylamino group. Another particularly preferred sub-group of compounds of the general formula I is that in which $R^2$ represents hydrogen, methyl, ethyl, propyl, butyl, phenyl or cyclopropylmethyl or in which $R^1$ and $R^2$ together represent a ethylene chain.

Further preferred subgroups of the general formula I are those in which $R^4$ represents methyl, ethyl or phenyl, in which $R^5$ represents hydrogen, methyl, trifluoromethyl, ethyl, propyl, butyl, phenyl or cyclopropyl, and in which $R^6$ represents hydrogen or methyl.

The present invention also provides a process for the preparation of compounds of the general formula I as defined hereinbefore, which comprises reacting a compound of the general formula II, or an activated derivative thereof,

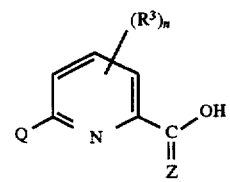

in which $R^3$ and n are as defined hereinbefore, and Q represents a leaving group or a group

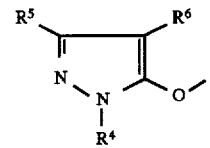

in which the substituents are as defined hereinbefore, with a compound of the general formula III

    III in which the substituents are as defined hereinbefore, and, in the case that Q represents a leaving group, followed by reaction of the product obtained with a compound of the general formula IV

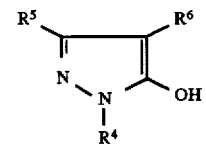

in which the substituents are defined hereinbefore, while in the case that $R^1$ and/or $R^2$ represent a hydrogen atom, this hydrogen atom may be exchanged by another substituent within the definition of $R^1$ and/or $R^2$ by reaction with a suitable agent such as an alkylating agent.

A leaving group is any group that will, under the reaction conditions, cleave from the starting material, thus enabling substitution at that specific site. The leaving group Q may suitably be a halogen atom, for example a bromine atom or, especially, a chlorine atom, an alkoxy group, suitably $C_{1-4}$ alkoxy, especially methoxy, an alkyl- or aryl-sulphonium group, especially a $C_{1-6}$ alkyl-, phenyl- or tolyl-sulphonium group, or an alkyl- or aryl-sulphonic acid group, especially a $C_{1-6}$ alkyl-, phenyl- or tolyl-sulphonium group.

Activated derivatives of the compounds of the general formula II are compounds in which the hydroxy group of the acid function has been replaced by a suitable leaving group, for instance a halogen atom, for example a bromine atom, or especially, a chlorine atom, an alkoxy group, suitably $C_{1-4}$ alkoxy, especially methoxy, or an imidazole group.

The process is suitably carried out in the presence of an organic solvent, for example dimethylformamide or dimethylsulphoxide, or an aromatic hydrocarbon, for example benzene or toluene, or a halogenated hydrocarbon, for example dichloromethane, or an ether, for example diethyl ether, or an ester, for example ethyl acetate.

The process is suitably carried out at a temperature in the range of 0° to 100° C., preferably at the reflux temperature of the reaction mixture, and suitably in the presence of a base, for example potassium hydroxide, and a copper catalyst, such as cuprous chloride.

Suitably the reaction is carried out using substantially equimolar amounts of the reactants. However, it can be expedient to use one reactant in excess.

Compounds of the general formula I in which Z represents a sulphur atom are suitably prepared by reaction of a compound of the general formula I, or a precursor thereof, later on followed by one or more additional reactions, in which Z represents an oxygen atom, with phosphorous pentasulphide under standard reaction conditions, for example by heating, suitably under reflux, in the presence of an inert organic solvent, suitably an organic solvent, for example benzene, toluene, pyridine or quinoline.

The compounds of the present invention may be isolated and purified by conventional techniques, for example by solvent extraction, evaporation followed by recrystallisation or by chromatography on for example silica or alumina.

The conversion of a resultant compound of the general formula I into a further compound of the general formula I may suitably be carried out by reaction with an alkyl halide. Suitably the alkyl halide is an alkyl iodide, bromide or chloride.

The compound of the general formula

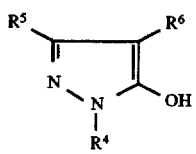

in which the substituents are defined hereinbefore are either commercially available or may be prepared as described in the literature, for example in J. Het. Chem. 28 (1991), p. 1971ff, and J. Het. Chem. 27 (1990), p. 243ff. For the synthesis of chloropicolinic acid reference is made to J. Pharm. Belg. 35 (1980), 5–11.

The reaction of the compounds obtained by reaction of compounds of the general formula II in which Q represents a leaving group, with a substituted hydroxypyrazole is suitably carried out in the presence of an organic solvent, for example dimethylformamide or dimethylsulphoxide, or an aromatic hydrocarbon, for example benzene or toluene, or a halogenated hydrocarbon, for example dichloromethane, or an ether, for example diethyl ether, or an ester, for example ethyl acetate. The process is suitably carried out at a temperature in the range of 0° to 100° C., preferably at the reflux temperature of the reaction mixture, and suitably in the presence of a base, for example potassium hydroxide, and a copper catalyst, such as cuprous chloride.

Activated derivatives of compounds of the general formula II may be prepared from the corresponding acids by standard methods for the preparation of, for example, esters, using, for example alcohols and acid catalysts or thionyl chloride, or of acid chlorides and bromides, using, for example, thionyl chloride or thionyl bromide, or of imidazole derivatives, using, for example, carbonyl diimidazole. The acid compounds themselves can be prepared by standard methods from chloropicolinic acid or esters thereof.

The substituted amines of the general formula III are either known or can be prepared by standard techniques.

Compounds of the general formula II in which Z represents an oxygen atom and Q is the group

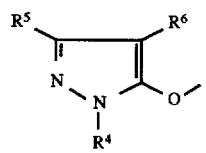

(further indicated as general formula VI) may suitably be prepared by hydrolysis of compounds of the general formula V

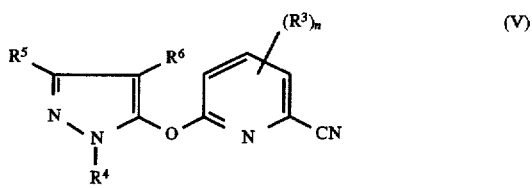

in which $R^3$ to $R^6$ and n are as defined above. This reaction is suitably carried out in the presence of a solvent such as water or ethylene glycol, using as reactants acids such as hydrochloric acid, sulphuric acid or bases such as potassium or sodium hydroxide, at a temperature in the range of 0°–150° C.

Compounds of the general formula V have been found to exhibit herbicidal activity and form another aspect of the invention.

Compounds of general formula V may be prepared by reaction of a compound of the general formula

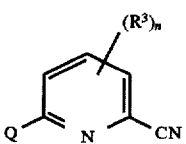

in which Q is as defined above, with a compound of the general formula

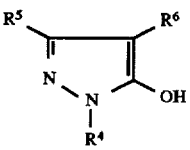

in which the substituents are as defined above.

The process is suitably carried out in the presence of an organic solvent, for example dimethylformamide, preferably at the reflux temperature of the reaction mixture, and suitably in the presence of a base, for example potassium carbonate.

The compounds of the invention have been found to have a surprisingly high herbicidal activity with a wide spectrum of activity against grasses and, especially, broadleaved weeds. Examples have been found to show selectivity to cereals, for example maize, wheat, barley and rice, and to broad-leaved crops, for example soya, sunflower and cotton.

indicating that they may be useful in combating weeds growing in such crops.

The invention further provides a herbicidal composition comprising a compound of formula I or a compound of formula V as defined above in association with a carrier, and a method of making such a composition which comprises bringing a compound of formula I or a compound of formula V into association with a carrier.

The invention also provides the use of such a compound or composition according to the invention as a herbicide. Further in accordance with the invention there is provided a method of combating undesired plant growth at a locus by treating the locus with a compound or composition according to the invention. Application to the locus may be pre-emergence or post-emergence. The dosage of active ingredient used, may, for example, be in the range of from 0.01 to 10 kg/ha, suitably 0.05 to 4 kg/ha. The locus may, for example, be the soil or plants in a crop area, typical crops being cereals such as wheat and barley, and broad-leaved crops, such as soya, sunflower and cotton.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example compounds possessing insecticidal or fungicidal properties or other herbicides.

The following Examples illustrate the invention; Examples 1 to 9 illustrate the preparation of intermediates of general formula IV; Examples 41 to 52 illustrate the preparation of intermediates of general formula V; Examples 53 to 59 illustrate the preparation of intermediates of general formula VI; and Examples 10 to 40 and 60 to 177 illustrate the preparation of compounds of general formula I. All structures were confirmed by mass spectroscopy and/or 300'H nmr.

EXAMPLE 1

Preparation of N-(4-fluorophenyl)-2-chloro-6-pyridinecarboxamide

6-Chloropicolinic acid (25 g) in 50 ml thionyl chloride was stirred and heated to reflux for two hours. The excess thionyl chloride was evaporated in vacuo and 200 ml diethylether was added to the residual 6-chloropicolinoyl chloride. A solution of 18.5 g 4-fluoroaniline in 20 ml diethylether was added with stirring, maintaining the temperature below 20°. After the addition, the reaction mixture was stirred overnight at ambient temperature. 100 ml of water was added to the reaction mixture and the organic layer separated. After a further washing with water and drying with anhydrous magnesium sulphate, the solvent was removed in vacuo to give the title compound (30 g, 75%) as a pale brown solid of mp 98°.

EXAMPLES 2 TO 9

By methods analogous to that of example 1, further compounds of the general formula IV were prepared by reaction of compounds of the general formula III with 6-chloropicolinic acid. Details are given in Table I.

TABLE I (IV)

| Example No. | $R^1$ | $R^2$ | mp (°C.) | Yield (%) |
|---|---|---|---|---|
| 2 | phenyl | H | 90 | 87 |
| 3 | 2-F-phenyl | H | 88 | 91 |
| 4 | $CH_2CF_3$ | H | 82 | 95 |
| 5 | $i\text{-}C_3H_7$ | H | oil | 82 |
| 6 | cyclopropyl | H | 77 | 71 |
| 7 | $C_2H_5$ | H | oil | 88 |

TABLE I-continued (IV)

| Example No. | $R^1$ | $R^2$ | mp (°C.) | Yield (%) |
|---|---|---|---|---|
| 8 | $2,4\text{-}F_2\text{-phenyl}$ | H | 102 | 69 |
| 9 | phenyl | $C_2H_5$ | oil | 52 |

EXAMPLE 10

Preparation of N-(4-fluorophenyl)-2-(1',3'-dimethylpyrazol-5'-yloxy)-6-pyridinecarboxamide 2.2 g of 1,3-dimethyl-5-hydroxypyrazol was added to a solution of 1.1 g potassium hydroxide in 40 ml methanol. The solvent was evaporated in vacuo after toluene was added to give the anhydrous potassium salt. The residue was resolved in 15 ml anhydrous N,N-dimethylformamide. After the addition of 5 g N-(4-fluorophenyl)-2-chloro-6-pyridinecarboxamide and 0.2 g CuCl the mixture was heated to reflux for 6 hours. After cooling, the reaction mixture was poured into 200 ml water and 200 ml ethyl acetate. The organic layer was separated and the aqueous phase extracted one more time with ethyl acetate. The combined extracts were dried with anhydrous magnesium sulphate and the solvent was removed in vacuo. The crude product was purified by flash silica gel column chromatography using hexane/ethyl acetate (7/3). The title compound was obtained as a white solid (2 g, 31%), mp 114°.

EXAMPLES 11 TO 40

By methods analogous to that of example 10, further compounds of the general formula I were prepared by reaction of compounds of the general formula IV with substituted 5-hydroxypyrazoles. Details are given in Table II.

TABLE II

| Example No. | R | $R^1$ | $R^2$ | mp (°C.) | Yield (%) |
|---|---|---|---|---|---|
| 11 | 1,3-$(CH_3)_2$-pyrazol-5-yloxy | phenyl | H | 115 | 62 |
| 12 | 1,3-$(CH_3)_2$-pyrazol-5-yloxy | 2-F-phenyl | H | 119 | 28 |
| 13 | 1,3-$(CH_3)_2$-pyrazol-5-yloxy | $CH_2CF_3$ | H | 105 | 34 |
| 14 | 1-$CH_3$-3-$nC_3H_7$-pyrazol-5-yloxy | $iC_3H_7$ | H | oil | 83 |
| 15 | 1-$CH_3$-3-$nC_3H_7$-pyrazol-5-yloxy | cyclopropyl | H | 56 | 80 |
| 16 | 1-$CH_3$-3-$nC_3H_7$-pyrazol-5-yloxy | $C_2H_5$ | H | oil | 41 |
| 17 | 1-$CH_3$-3-$nC_3H_7$-pyrazol-5-yloxy | $2,4\text{-}F_2$-phenyl | H | 100 | 78 |
| 18 | 1-$CH_3$-3-$nC_3H_7$-pyrazol-5-yloxy | phenyl | H | 115 | 80 |
| 19 | 1-$CH_3$-3-$nC_3H_7$-pyrazol-5-yloxy | $CH_2CF_3$ | H | 84 | 74 |
| 20 | 1-$CH_3$-3-$C_2H_5$-pyrazol-5-yloxy | $2,4\text{-}F_2$-phenyl | H | 95 | 67 |

TABLE II-continued

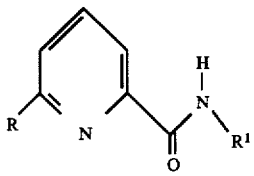

| Example No. | R | R¹ | R² | mp (°C.) | Yield (%) |
|---|---|---|---|---|---|
| 21 | 1-CH₃-3-C₂H₅-pyrazol-5-yloxy | CH₂CF₃ | H | 81 | 61 |
| 22 | 1-CH₃-3-C₂H₅-pyrazol-5-yloxy | phenyl | H | 109 | 78 |
| 23 | 1-CH₃-3-C₂H₅-pyrazol-5-yloxy | cyclopropyl | H | 95 | 35 |
| 24 | 1-CH₃-3-C₂H₅-pyrazol-5-yloxy | 4-F-phenyl | H | 104 | 92 |
| 25 | 1-CH₃-3-C₂H₅-pyrazol-5-yloxy | iC₃H₇ | H | oil | 59 |
| 26 | 1-CH₃-3-C₂H₅-pyrazol-5-yloxy | C₂H₅ | H | oil | 30 |
| 27 | 1-CH₃-3-C₂H₅-pyrazol-5-yloxy | CH₂C(CH₃)=CH₂ | H | 51 | 43 |
| 28 | 1-CH₃-3-iC₃H₇-pyrazol-5-yloxy | 4-F-phenyl | H | 105 | 88 |
| 29 | 1-CH₃-3-iC₃H₇-pyrazol-5-yloxy | 2,4-F₂-phenyl | H | 97 | 81 |
| 30 | 1-CH₃-3-iC₃H₇-pyrazol-5-yloxy | phenyl | H | 112 | 80 |
| 31 | 1-CH₃-3-iC₃H₇-pyrazol-5-yloxy | cyclopropyl | H | 64 | 30 |
| 32 | 1-CH₃-3-iC₃H₇-pyrazol-5-yloxy | iC₃H₇ | H | oil | 82 |
| 33 | 1-CH₃-3-iC₃H₇-pyrazol-5-yloxy | C₂H₅ | H | 57 | 56 |
| 34 | 1-CH₃-3-iC₃H₇-pyrazol-5-yloxy | CH₂CF₃ | H | 78 | 47 |
| 35 | 1-CH₃-3-iC₃H₇-pyrazol-5-yloxy | CH₂C(CH₃)=CH₂ | H | oil | 76 |
| 36 | 1-CH₃-3-iC₃H₇-pyrazol-5-yloxy | CH₂C(CH₃)=CH₂ | H | 38 | 32 |
| 37 | 1-CH₃-3-cyclopropyl-pyrazol-5-yloxy | 4-F-phenyl | H | 139 | 45 |
| 38 | 1-CH₃-3-nC₃H₇-pyrazol-5-yloxy | C₂H₅ | phenyl | 69 | 77 |
| 39 | 1-CH₃-3-C₂H₅-pyrazol-5-yloxy | C₂H₅ | phenyl | 83 | 40 |
| 40 | 1-CH₃-3-iC₃H₇-pyrazol-5-yloxy | C₂H₅ | phenyl | 62 | 44 |

EXAMPLE 41

Preparation of 2-(1',3'-dimethyl-pyrazol-5-yloxy)-pyridine-6-carbonitrile 5.6 g of 1,3-dimethyl-5-hydroxypyrazole (50 mmol) was added to a suspension of 7.7 g 2-chloro-6-cyanopyridine (55 mmol) and 7.6 g K₂CO₃ (55 mmol) in 50 ml N,N-dimethylformamide and heated to reflux with vigorous stirring for 5 hours. After cooling, the mixture was poured into water (100 ml) and the aqueous layer extracted 3 times with each 100 ml ethyl acetate. The combined extracts were dried with anhydrous magnesium sulphate and the solvent was removed in vacuo. The residue was purified by flash silica gel column chromatography using hexane/ethyl acetate 7/3. The title compound was obtained after recrystallisation from isopropanol as 5.9 g (55%) of white crystals of m.p. 95° C.

EXAMPLES 42 TO 52

By methods analogous to that of Example 41, further compounds of the general formula V were prepared by reaction of substituted 5-hydroxypyrazoles with 2-chloro-6-cyanopyridine. Details are given in Table III.

TABLE III

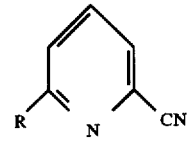

| Example No | R | mp (°C.) | Yield (%) |
|---|---|---|---|
| 42 | 1-CH₃-3-CF₃-pyrazol-5-yloxy | 112 | 72 |
| 43 | 1-CH₃-3-phenyl-pyrazol-5-yloxy | 109 | 66 |
| 44 | 1-(3-Cl-phenyl)-3-CH₃-pyrazol-5-yloxy | 95 | 24 |
| 45 | 1-CH₃-3-nC₃H₇-pyrazol-5-yloxy | 80 | 64 |
| 46 | 1-CH₃-3-tC₄H₉-pyrazol-5-yloxy | 81 | 82 |
| 47 | 1-phenyl-3-CH₃-pyrazol-5-yloxy | 109 | 58 |
| 48 | 1,3-(phenyl)₂-pyrazol-5-yloxy | 124 | 18 |
| 49 | 1-phenyl-3-CF₃-pyrazol-5-yloxy | 165 | 62 |
| 50 | 1-phenyl-3,4-(CH₃)₂-pyrazol-5-yloxy | 82 | 34 |
| 51 | 1,3,4-(CH₃)₃-pyrazol-5-yloxy | 92 | 64 |
| 52 | 1-C₂H₅-3-CF₃-pyrazol-5-yloxy | 95 | 83 |

EXAMPLE 53

Preparation of 2-(1',3'-dimethyl-pyrazol-5-yloxy)-pyridine-6-carboxylic acid 2-(1',3'-dimethyl-pyrazol-5-yloxy)-pyridine-6-carbonitrile (25 g, 0.11 mol) (from Example 41) were suspended in concentrated hydrochloric acid (100 ml) and heated to reflux for 30 minutes. After cooling, the mixture was diluted with 400 ml of water to precipitate the title compound as a white solid (14.1 g, 52%), mp 182° C.

EXAMPLES 54 TO 59

By methods analogous to that of example 53, further compounds of the general formula VI were prepared by hydrolysis of compounds of the general formula V. Details are given in Table IV.

TABLE IV

VI

R—/\—COOH
    N

| Example No | R | mp (°C.) | Yield (%) |
|---|---|---|---|
| 54 | 1-CH$_3$-3-CF$_3$-pyrazol-5-yloxy | 161 | 40 |
| 55 | 1-CH$_3$-3-phenyl-pyrazol-5-yloxy | 161 | 50 |
| 56 | 1-phenyl-3-CH$_3$-pyrazol-5-yloxy | 156 | 50 |
| 57 | 1-phenyl-3,4-(CH$_3$)$_2$-pyrazol-5-yloxy | 165 | 50 |
| 58 | 1-CH$_3$-3-tC$_4$H$_9$-pyrazol-5-yloxy | 145 | 25 |
| 59 | 1-C$_2$H$_5$-3-CF$_3$-pyrazol-5-yloxy | 163 | 67 |

EXAMPLE 60

Preparation of N-(4-fluorophenyl)-2-(1'-methyl-3'-trifluoro-methyl-pyrazol-5-yloxy)-6-pyridinecarboxamide (Method A)

2-(1'-methyl-3'-trifluoromethyl-pyrazol-5-yloxy)-pyridine-6-carboxylic acid (2.9 g, 10 mmol) (from Example 54) in thionyl chloride was heated to reflux for 30 minutes. The excess thionyl chloride was evaporated in vacuo and acetonitrile (30 ml) was added to the residue. A solution of 4-fluoroaniline (1.1 ml, 11 mmol) and triethylamine (3 ml) was added with stirring at ambient temperature and the mixture was left overnight. The solvent was evaporated in vacuo and the residue resolved in ethyl acetate (50 ml). After extracting with dilute aqueous sodium hydroxide, the organic layer was dried with anhydrous magnesium sulphate. The solvent was removed in vacuo and the crude product purified by flash silica gel column chromatography using hexane/ethyl acetate 1/1. The title compound was obtained as a white solid (2.9 g, 76%), mp 136° C.

EXAMPLES 61 TO 109

By methods analogous to that of Example 60, further compounds of the general formula I in which R$^2$ represents hydrogen were prepared by conversion of compounds of the general formula VI into activated derivatives thereof and then reaction with compounds of the general formula III. Details are given in Table V.

TABLE V

| Ex. No. | R | R$^1$ | mp (°C.) | Yield (%) |
|---|---|---|---|---|
| 61 | 1-CH$_3$-3-phenyl-pyrazol-5-yloxy | 3-F-phenyl | 140 | 16 |
| 62 | 1-CH$_3$-3-CF$_3$-pyrazol-5-yloxy | phenyl | 127 | 55 |
| 63 | 1-CH$_3$-3-CF$_3$-pyrazol-5-yloxy | 3-F-phenyl | 153 | 71 |
| 64 | 1-CH$_3$-3-CF$_3$-pyrazol-5-yloxy | CH$_2$CH=CH$_2$ | oil | 64 |
| 65 | 1-CH$_3$-3-CF$_3$-pyrazol-5-yloxy | CH$_2$CF$_3$ | oil | 69 |
| 66 | 1-CH$_3$-3-CF$_3$-pyrazol-5-yloxy | 2,4-F$_2$-phenyl | 150 | 75 |
| 67 | 1-CH$_3$-3-CF$_3$-pyrazol-5-yloxy | nC$_3$H$_7$ | 86 | 63 |
| 68 | 1-CH$_3$-3-CF$_3$-pyrazol-5-yloxy | iC$_3$H$_7$ | 83 | 84 |
| 69 | 1-CH$_3$-3-CF$_3$-pyrazol-5-yloxy | iC$_4$H$_9$ | 84 | 83 |
| 70 | 1-CH$_3$-3-CF$_3$-pyrazol-5-yloxy | sC$_4$H$_9$ | 57 | 56 |
| 71 | 1-CH$_3$-3-CF$_3$-pyrazol-5-yloxy | CH$_2$CH$_2$Cl | 103 | 34 |
| 72 | 1-CH$_3$-3-CF$_3$-pyrazol-5-yloxy | CH$_2$CN | 151 | 36 |
| 73 | 1-CH$_3$-3-CF$_3$-pyrazol-5-yloxy | cyclopentyl | 119 | 45 |
| 74 | 1-CH$_3$-3-CF$_3$-pyrazol-5-yloxy | CH$_2$CH$_2$OCH$_3$ | 60 | 58 |
| 75 | 1-CH$_3$-3-CF$_3$-pyrazol-5-yloxy | C(CH$_3$)$_2$C≡CH | 64 | 68 |
| 76 | 1-CH$_3$-3-CF$_3$-pyrazol-5-yloxy | CH$_3$ | 92 | 35 |
| 77 | 1-CH$_3$-3-CF$_3$-pyrazol-5-yloxy | 2',2'-Cl$_2$-cyclo-propyl-CH$_2$ | 109 | 69 |
| 78 | 1-CH$_3$-3-CF$_3$-pyrazol-5-yloxy | CH$_2$C≡CH | 86 | 62 |
| 79 | 1-CH$_3$-3-CF$_3$-pyrazol-5-yloxy | C$_2$H$_5$ | 89 | 54 |
| 80 | 1-CH$_3$-3-phenyl-pyrazol-5-yloxy | phenyl | 199 | 12 |
| 81 | 1-CH$_3$-3-phenyl-pyrazol-5-yloxy | 2,4-F$_2$-phenyl | 135 | 63 |
| 82 | 1-CH$_3$-3-phenyl-pyrazol-5-yloxy | cyclopropyl | 112 | 14 |
| 83 | 1-CH$_3$-3-CF$_3$-pyrazol-5-yloxy | nC$_4$H$_9$ | 67 | 56 |
| 84 | 1-CH$_3$-3-CF$_3$-pyrazol-5-yloxy | nC$_5$H$_{11}$ | 62 | 51 |

TABLE V-continued

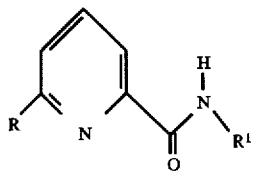

| Ex. No. | R | R¹ | mp (°C.) | Yield (%) |
|---|---|---|---|---|
| 85 | 1-$CH_3$-3-$CF_3$-pyrazol-5-yloxy | 3,4-$F_2$-phenyl | 140 | 60 |
| 86 | 1-$CH_3$-3-$CF_3$-pyrazol-5-yloxy | t$C_4H_9$O | 108 | 12 |
| 87 | 1-$CH_3$-3-$CF_3$-pyrazol-5-yloxy | $CH_2(CH_3)_3$ | 89 | 43 |
| 88 | 1-$CH_3$-3-t$C_4H_9$-pyrazol-5-yloxy | $CH_2CF_3$ | 93 | 39 |
| 89 | 1-$CH_3$-3-phenyl-pyrazol-5-yloxy | s$C_4H_9$ | 68 | 9 |
| 90 | 1-$CH_3$-3-phenyl-pyrazol-5-yloxy | i$C_3H_7$ | 82 | 6 |
| 91 | 1-$CH_3$-3-phenyl-pyrazol-5-yloxy | $CH_2CF_3$ | 147 | 50 |
| 92 | 1-$CH_3$-3-t$C_4H_9$-pyrazol-5-yloxy | 4-F-phenyl | 104 | 58 |
| 93 | 1-$CH_3$-3-n$C_3H_7$-pyrazol-5-yloxy | 4-F-phenyl | 120 | 39 |
| 94 | 1,3,4-$(CH_3)_3$-pyrazol-5-yloxy | 4-F-phenyl | 125 | 46 |
| 95 | 1,3,4-$(CH_3)_3$-pyrazol-5-yloxy | cyclopropyl | oil | 14 |
| 96 | 1,4-$(CH_3)_2$-pyrazol-5-yloxy | 4-F-phenyl | 132 | 41 |
| 97 | 1-$C_2H_5$-3-$CF_3$-pyrazol-5-yloxy | 4-F-phenyl | 116 | 65 |
| 98 | 1-$C_2H_5$-3-$CF_3$-pyrazol-5-yloxy | phenyl | 126 | 41 |
| 99 | 1-$C_2H_5$-3-$CF_3$-pyrazol-5-yloxy | cyclopropyl | 80 | 52 |
| 100 | 1-$C_2H_5$-3-$CF_3$-pyrazol-5-yloxy | s$C_4H_9$ | oil | 63 |
| 101 | 1-$CH_3$-3-$CF_3$-pyrazol-5-yloxy | cyclopropyl-$CH_2$ | 78 | 71 |
| 102 | 1-$C_2H_5$-3-$CF_3$-pyrazol-5-yloxy | cyclobutyl | 45 | 27 |
| 103 | 1-$CH_3$-3-$CF_3$-pyrazol-5-yloxy | cyclobutyl | 93 | 40 |
| 104 | 1-$CH_3$-3-$CF_3$-pyrazol-5-yloxy | $CH_2C(CH_3)=CH_2$ | oil | 67 |
| 105 | 1-$CH_3$-3-t$C_4H_9$-pyrazol-5-yloxy | cyclopropyl | oil | 73 |
| 106 | 1-$CH_3$-3-t$C_4H_9$-pyrazol-5-yloxy | i$C_3H_7$ | oil | 76 |
| 107 | 1-$CH_3$-3-t$C_4H_9$-pyrazol-5-yloxy | $C_2H_5$ | oil | 26 |
| 108 | 1-$CH_3$-3-t$C_4H_9$-pyrazol-5-yloxy | phenyl | 104 | 40 |
| 109 | 1-$CH_3$-3-t$C_4H_9$-pyrazol-5-yloxy | 2,4-$F_2$-phenyl | 133 | 54 |

EXAMPLES 110 TO 114

By methods analogous to that of example 60, further compounds of the general formula I were prepared by conversion of compounds of the general formula VI into activated derivatives thereof and then reaction with compounds of the general formula III. Details are given in Table VI.

TABLE VI

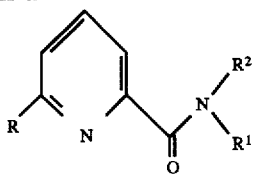

| Example No. | R | R¹/R² | mp (°C.) | Yield (%) |
|---|---|---|---|---|
| 110 | 1-$CH_3$-3-$CF_3$-pyrazol-5-yloxy | $CH_3/CH_3$ | oil | 57 |
| 111 | 1-$CH_3$-3-$CF_3$-pyrazol-5-yloxy | $C_2H_5/C_2H_5$ | 74 | 44 |
| 112 | 1-$CH_3$-3-$CF_3$-pyrazol-5-yloxy | —$CH_2CH_2$— (cyclo) | 71 | 21 |
| 113 | 1-$CH_3$-3-$CF_3$-pyrazol-5-yloxy | n$C_3H_7$/cyclopropyl-$CH_2$ | oil | 64 |
| 114 | 1-$CH_3$-3-t$C_4H_9$-pyrazol-5-yloxy | $C_2H_5$/phenyl | 85 | 24 |

EXAMPLE 115

Preparation of N-(3-fluorophenyl)-2-(1',3'-dimethyl-pyrazol-5-yloxy)-6-pyridine-carboxamide (Method B)

To a solution of 2-(1',3'-dimethyl-pyrazol-5-yloxy)-pyridine-6-carboxylic acid (2.2 g, 9.6 mmol) (from Example 53) in anhydrous tetrahydrofuran (20 ml) was added carbonyldiimidazole (1.6 g, 10.6 mmol) and stirred for 30 minutes, maintaining the temperature up to 40° C. 3-fluoroaniline (1.1 ml, 10.6 mmol) was added and the reaction mixture heated to 50° C. After 2 hours, the clear mixture was poured into water (100 ml) and extracted three times with ethyl acetate (50 ml each). The combined extracts were dried with anhydrous magnesium sulphate and the solvent was removed in vacuo. The crude product was purified by flash silica gel column chromatography using hexane/ethyl acetate 1/1. The title compound was obtained as a white solid (1.7 g, 54%), mp 110° C.

EXAMPLES 116 TO 126

By methods analogous to that of Example 115, further compounds of the general formula I in which R² represents hydrogen were prepared by conversion of compounds of the general formula VI into activated derivatives thereof and then reaction with compounds of the general formula $NH_2R^1$. Details are given in Table VII.

TABLE VII

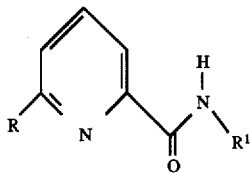

| Ex. No. | R | R¹ | mp (°C.) | Yield (%) |
|---|---|---|---|---|
| 116 | 1-$CH_3$-3-$CF_3$-pyrazol-5-yloxy | cyclopropyl | 117 | 76 |
| 117 | 1,3-$(CH_3)_2$-pyrazol-5-yloxy | cyclopropyl | 106 | 46 |
| 118 | 1,3-$(CH_3)_2$-pyrazol-5-yloxy | 2,4-$F_2$-phenyl | 114 | 54 |
| 119 | 1-$CH_3$-3-phenyl-pyrazol-5-yloxy | 4-F-phenyl | 131 | 44 |
| 120 | 1-phenyl-3-$CH_3$-pyrazol-5-yloxy | 3-F-phenyl | 134 | 70 |
| 121 | 1,3-$(CH_3)_2$-pyrazol-5-yloxy | $CH_2CH=CH_2$ | 76 | 22 |
| 122 | 1-$CH_3$-3-$CH_3$-pyrazol-5-yloxy | $iC_4H_9$ | 93 | 26 |
| 123 | 1-$CH_3$-3-phenyl-pyrazol-5-yloxy | $n-C_3H_7$ | oil | 21 |
| 124 | 1-phenyl-3,4-$(CH_3)_2$-pyrazol-5-yloxy | phenyl | 76 | 48 |
| 125 | 1-phenyl-3,4-$(CH_3)_2$-pyrazol-5-yloxy | 4-F-phenyl | 147 | 77 |
| 126 | 1-$CH_3$-3-phenyl-pyrazol-5-yloxy | $CH_2CH=CH_2$ | oil | 25 |

EXAMPLE 127

Preparation of N-(4-fluorophenyl)-N-methyl-2-(1'-methyl-3'-trifluoromethylpyrazol-5'-yloxy)-6-pyridinecarboxamide Sodium hydride (0.12 g, 3 mmol) was added to a stirred solution of N-(4-fluorophenyl)-2-(1'-methyl-3'-trifluoromethylpyrazol-5'-yloxy)-6-pyridinecarboxamide (1.14 g, 3 mmol) (from Example 60) in anhydrous tetrahydrofuran (10 ml). After gas evolution has ceased, methyl iodide (0.37 ml, 6 mmol) was added and the mixture was heated to reflux for 10 minutes. After cooling, the mixture was poured into water (50 ml) and ethyl acetate (50 ml). The organic layer was separated and the aqueous phase was extracted in addition with ethyl acetate (50 ml). The combined extracts were dried with anhydrous magnesium sulphate and the solvent was removed in vacuo. The crude product was purified by flash silica gel column chromatography using hexane/ethyl acetate 1/1. The title compound was obtained as a yellow glassy oil (0.8 g, 68%).

EXAMPLES 128 TO 169

By methods analogous to that of Example 127, further compounds of the general formula I were prepared by conversion of compounds of the general formula I in which $R^2$ represents hydrogen. Details are given in Table VIII.

TABLE VIII

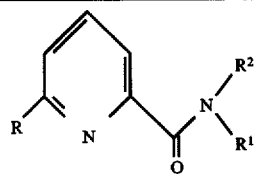

| Ex. No. | R | R¹/R² | mp (°C.) | Yield (%) |
|---|---|---|---|---|
| 128 | 1-$CH_3$-3-$CF_3$-pyrazol-5-yloxy | cycloprop./$CH_3$ | oil | 73 |
| 129 | 1-$CH_3$-3-$CF_3$-pyrazol-5-yloxy | cycloprop./$C_2H_5$ | oil | 38 |
| 130 | 1,3-$(CH_3)_2$-pyrazol-5-yloxy | phenyl/$CH_3$ | oil | 45 |
| 131 | 1,3-$(CH_3)_2$-pyrazol-5-yloxy | 3-F-phenyl/$CH_3$ | oil | 75 |
| 132 | 1,3-$(CH_3)_2$-pyrazol-5-yloxy | 4-F-phenyl/$CH_3$ | oil | 75 |
| 133 | 1,3-$(CH_3)_2$-pyrazol-5-yloxy | cycloprop./$CH_3$ | oil | 48 |
| 134 | 1,3-$(CH_3)_2$-pyrazol-5-yloxy | 2,4-$F_2$-phenyl/$CH_3$ | oil | 48 |
| 135 | 1-$CH_3$-3-$CF_3$-pyrazol-5-yloxy | 2,4-$F_2$-phenyl/$C_2H_5$ | 78 | 56 |
| 136 | 1-$CH_3$-3-$CF_3$-pyrazol-5-yloxy | 4-F-phenyl/$C_2H_5$ | 87 | 69 |
| 137 | 1-$CH_3$-3-$CF_3$-pyrazol-5-yloxy | phenyl/$CH_3$ | 71 | 74 |
| 138 | 1-$CH_3$-3-$CF_3$-pyrazol-5-yloxy | phenyl/$C_2H_5$ | 92 | 77 |
| 139 | 1-$CH_3$-3-$CF_3$-pyrazol-5-yloxy | 3-F-phenyl/$CH_3$ | oil | 61 |
| 140 | 1-$CH_3$-3-$CF_3$-pyrazol-5-yloxy | $CH_2CH=CH_2$/$CH_3$ | oil | 71 |
| 141 | 1-$CH_3$-3-$CF_3$-pyrazol-5-yloxy | $CH_2CF_3$/$CH_3$ | oil | 90 |
| 142 | 1-$CH_3$-3-$CF_3$-pyrazol-5-yloxy | $CH_2CF_3$/$C_2H_5$ | oil | 70 |
| 143 | 1-$CH_3$-3-$CF_3$-pyrazol-5-yloxy | 2,4-$F_2$-phenyl/$CH_3$ | 108 | 82 |
| 144 | 1-$CH_3$-3-$CF_3$-pyrazol-5-yloxy | $nC_3H_7$/$CH_3$ | oil | 68 |
| 145 | 1-$CH_3$-3-$CF_3$-pyrazol-5-yloxy | $nC_3H_7$/$C_2H_5$ | oil | 49 |
| 146 | 1-$CH_3$-3-$CF_3$-pyrazol-5-yloxy | $iC_3H_7$/$CH_3$ | oil | 76 |
| 147 | 1-$CH_3$-3-$CF_3$-pyrazol-5-yloxy | $iC_3H_7$/$C_2H_5$ | oil | 36 |
| 148 | 1-$CH_3$-3-$CF_3$-pyrazol-5-yloxy | $iC_4H_9$/$CH_3$ | oil | 73 |
| 149 | 1-$CH_3$-3-$CF_3$-pyrazol-5-yloxy | $iC_4H_9$/$CH_2CH_3$ | oil | 40 |
| 150 | 1-$CH_3$-3-$CF_3$-pyrazol-5-yloxy | $sC_4H_9$/$CH_3$ | oil | 47 |
| 151 | 1-$CH_3$-3-$CF_3$-pyrazol-5-yloxy | $sC_4H_9$/$C_2H_5$ | oil | 39 |
| 152 | 1-phenyl-3-$CH_3$-pyrazol-5-yloxy | 4-F-phenyl/$C_2H_5$ | 100 | 46 |
| 153 | 1-phenyl-3-$CH_3$-pyrazol-5-yloxy | 2,4-$F_2$-phenyl/$C_2H_5$ | oil | 27 |
| 154 | 1-phenyl-3-$CH_3$-pyrazol-5-yloxy | 3-F-phenyl/$C_2H_5$ | 105 | 26 |
| 155 | 1-phenyl-3-$CH_3$-pyrazol-5-yloxy | phenyl/$CH_3$ | oil | 34 |
| 156 | 1,3-$(CH_3)_2$-pyrazol-5-yloxy | $iC_4H_9$/$CH_3$ | oil | 44 |
| 157 | 1-$CH_3$-3-$CF_3$-pyrazol-5-yloxy | $nC_3H_7$/$nC_3H_7$ | 73 | 65 |
| 158 | 1-$CH_3$-3-$CF_3$-pyrazol-5-yloxy | $C_2H_5$/$CH_3$ | oil | 30 |
| 159 | 1-$CH_3$-3-$CF_3$-pyrazol-5-yloxy | 2',2'-$Cl_2$ cyclopropyl/$CH_3$ | 109 | 57 |
| 160 | 1-$CH_3$-3-$CF_3$-pyrazol-5-yloxy | cyclopentyl/$CH_3$ | oil | 68 |
| 161 | 1-$CH_3$-3-phenyl-pyrazol-5-yloxy | $CH_2CF_3$/$CH_3$ | oil | 69 |
| 162 | 1-$CH_3$-3-phenyl-pyrazol-5-yloxy | phenyl/$CH_3$ | 142 | 70 |
| 163 | 1-$CH_3$-3-phenyl-pyrazol-5-yloxy | phenyl/$C_2H_5$ | 115 | 51 |
| 164 | 1-$CH_3$-3-$tC_4H_9$-pyrazol-5-yloxy | 4-F-phenyl/$CH_3$ | oil | 75 |
| 165 | 1-$CH_3$-3-$nC_3H_7$-pyrazol-5-yloxy | 4-F-phenyl/$CH_3$ | oil | 79 |
| 166 | 1,3,4-$(CH_3)_3$-pyrazol-5-yloxy | 4-F-phenyl/$CH_3$ | 116 | 40 |
| 167 | 1,3,4-$(CH_3)_3$-pyrazol-5-yloxy | 4-F-phenyl/$C_2H_5$ | oil | 41 |
| 168 | 1-$CH_3$-3-$CF_3$-pyrazol-5-yloxy | $CH_3$/$tC_4H_9$ | 81 | 32 |
| 169 | 1-$CH_3$-3-$CF_3$-pyrazol-5-yloxy | $CH_2CH=CH_2$/phenyl | 77 | 42 |

EXAMPLES 170 TO 175

By methods analogous to that of example 60, further compounds of the general formula I in which $R^2$ represents hydrogen were prepared by reaction of compounds of the general formula $H_2NNR^7R^8$ with compounds of the general formula VI. Details are given in Table IX.

TABLE IX

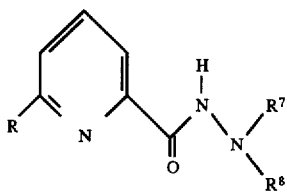

| Ex. No. | R | R⁷/R⁸ | mp (°C.) | Yield (%) |
|---|---|---|---|---|
| 170 | 1-CH₃-3-CF₃-pyrazol-5-yloxy | H/phenyl | 151 | 48 |
| 171 | 1-CH₃-3-CF₃-pyrazol-5-yloxy | CH₃/CH₃ | 101 | 18 |
| 172 | 1-CH₃-3-CF₃-pyrazol-5-yloxy | H/CH₂CF₃ | 146 | 42 |
| 173 | 1-CH₃-3-CF₃-pyrazol-5-yloxy | H/3-F-phenyl | 141 | 46 |
| 174 | 1-CH₃-3-phenyl-pyrazol-5-yloxy | CH₃/CH₃ | 72 | 20 |
| 175 | 1-CH₃-3-phenyl-pyrazol-5-yloxy | H/tC₄H₉ | 110 | 5 |

EXAMPLE 176

Preparation of N-(4-fluorophenyl)-2-(1'-methyl-3'-trifluoromethylpyrazol-5-yloxy)-4-methyl-6-pyridinecarboxamide (a) Preparation of 6-amino-2-bromo-4-methylpyridine:

To a solution of 50 g 2-methyl-2-chloromethyloxirane in 23 ml concentrated hydrochloric acid at ice-bath temperature a solution of 27.4 g sodium cyanide in 23 ml hydrochloric acid was added. After stirring for 10 hours at that temperature the reaction mixture was warmed to 40° C. and a solution of 33.8 g potassium cyanide in 50 ml water was added. The resulting mixture was warmed to 50° C. and stirred for 4 hours. After cooling the solution was neutralized and extracted three times with 150 ml ethyl acetate each. The combined organic layers were dried with anhydrous magnesium sulphate. Removal of the solvent afforded 56.4 g (96%) of 1,3-dicyano-2-methyl-2-hydroxypropane. This crude material was sufficiently pure to be submitted directly to the following ring closure.

56.4 g of 1,3-dicyano-2-methyl-2-hydroxypropane was added carefully to a 33% solution of hydrogen bromide in glacial acetic acid at ice-bath temperature. The reaction mixture was then stirred for 3 days at ambient temperature. The solvent was removed in vacuo and the residual oil was brought to pH 12 with a 10 molar aqueous solution of sodium hydroxide. This alkaline solution was extracted three times each with 100 ml ethyl acetate. The combined organic layers were dried with magnesium sulphate and the solvent removed in vacuo. 56 g (66%) of 6-amino-2-bromo-4-methylpyridine was obtained as a colourless solid of melting point 99° C.

| Analysis: | | | |
|---|---|---|---|
| C calc.: | 38.5 | found: | 38.3 |
| H calc.: | 3.8 | found: | 3.6 |
| N calc.: | 15.0 | found: | 14.7 |

(b) Preparation of 2-bromo-6-chloro-4-methylpyridine:

A solution of 56 g 6-amino-2-bromo-4-methylpyridine in 500 ml of concentrated hydrochloric acid was cooled to −50° C. and saturated with gaseous HCl via a gas inlet. Under continuous cooling a solution of 25 g sodium nitrite in 60 ml water was added slowly. The reaction mixture was stirred for a further 2 hours at −50° C. The mixture was allowed to warm up to ambient temperature and set alkaline with a 50% aqueous solution of sodium hydroxide. The aqueous phase was extracted three times each with 200 ml dichloromethane. The combined extracts were dried with calcium chloride, and the solvent removed in vacuo to afford 22.5 g (40%) of 2-bromo-6-chloro-4-methylpyridine as a pale brown solid of melting point 76° C.

| Analysis: | | | |
|---|---|---|---|
| C calc.: | 34.9 | found: | 34.6 |
| H calc.: | 2.4 | found: | 2.2 |
| N calc.: | 6.8 | found: | 6.9 |

(c) Preparation of 2-chloro-6-cyano-4-methylpyridine:

To a solution of 20.7 g of 2-bromo-6-chloro-4-methylpyridine in 100 ml anhydrous N,N-dimethylformamide 9.9 g of copper cyanide was added. The reaction mixture was heated to reflux for 7 hours. After cooling, the mixture was filtered through a silica gel column with 500 ml ethyl acetate. The obtained solution was washed with a saturated aqueous solution of sodium chloride. The solvent was removed in vacuo and the residue purified by silica gel column chromatography using hexane/ethyl acetate 1:1. 7.6 g (54%) of the title compound was obtained as a white solid of melting point 133° C.

| Analysis: | | | |
|---|---|---|---|
| C calc.: | 51.3 | found: | 50.9 |
| H calc.: | 3.6 | found: | 3.5 |
| N calc.: | 19.9 | found: | 19.7 |

(d) Preparation of 2-(1'-methyl-3'-trifluoromethylpyrazol-5-yloxy)-6-cyano-4-methylpyridine 7.6 g 2-bromo-6-cyano-4-methylpyridine, 9 g 1-methyl-3-trifluoromethyl-5-hydroxypyrazole and 9.7 g potassium carbonate were mixed in 30 ml N,N-dimethylformamide and heated to reflux for 5 hours. After cooling, the reaction mixture was poured into 300 ml water and the aqueous layer extracted three times each with 100 ml ethyl acetate. The combined extracts were dried with anhydrous magnesium sulphate and the solvent removed in vacuo. Purification by silica gel column chromatography using hexane/ethyl acetate 7:3 afforded 8.1 g (50%) of the title compound as a pale brown solid of melting point 88° C.

| Analysis: | | | |
|---|---|---|---|
| C calc.: | 51.1 | found: | 51.0 |
| H calc.: | 3.2 | found: | 3.0 |
| N calc.: | 19.8 | found: | 19.7 |

(e) Preparation of 2-(1'-methyl-3'-trifluoromethylpyrazol-5-yloxy)-4-methyl-pyridine-6-carboxylic acid 100 ml of concentrated hydrochloric acid was mixed with 7.6 g of 2-(1'-methyl-3'-trtfluoromethylpyrazol-5-yloxy)-6-cyano-4-methylpyridine and heated to reflux for 6 hours. After cooling, the aqueous reaction mixture was extracted three times with 100 ml dichloromethane. The combined extracts were dried with anhydrous calcium chloride. Removal of the solvent in vacuo gave 6.3 g (77%) of the title compound with melting point 168° C.

| Analysis: | | | |
|---|---|---|---|
| C calc.: | 47.8 | found: | 47.6 |
| H calc.: | 3.3 | found: | 3.3 |
| N calc.: | 14.0 | found: | 14.2 |

The product of (e) above was then converted to the final product by the procedure of Example 60. Details of said final product and of a further compound prepared by an analogous method are given in Table X.

TABLE X

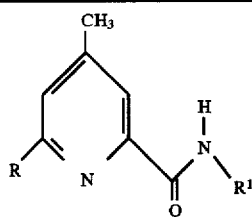

| Ex. No. | R | R¹ | mp (°C.) | Yield (%) |
|---|---|---|---|---|
| 176 | 1-CH₃-3-CF₃-pyrazol-5-yloxy | 4-F-phenyl | 154 | 56 |
| 177 | 1-CH₃-3-CF₃-pyrazol-5-yloxy | cyclopropyl | 110 | 33 |

Elemental analysis data for the above compounds are set out in Table XI below.

TABLE IX

| | Analysis (%) | | | | | |
|---|---|---|---|---|---|---|
| Ex. | C | | H | | N | |
| No. | Calc. | Found | Calc. | Found | Calc. | Found |
| 1 | 57.5 | 57.6 | 3.2 | 3.4 | 11.2 | 11.2 |
| 2 | 62.0 | 62.1 | 3.9 | 4.1 | 12.0 | 12.1 |
| 3 | 57.5 | 57.3 | 3.2 | 3.5 | 11.2 | 11.1 |
| 4 | 40.3 | 40.6 | 2.5 | 2.8 | 11.7 | 11.6 |
| 5 | 64.1 | 64.0 | 6.6 | 6.4 | 8.3 | 8.3 |
| 6 | 55.0 | 54.5 | 4.6 | 5.0 | 14.3 | 14.1 |
| 7 | 62.1 | 62.2 | 5.9 | 5.8 | 9.1 | 9.1 |
| 8 | 53.6 | 53.6 | 2.6 | 2.9 | 10.4 | 10.4 |
| 9 | 72.9 | 72.5 | 5.7 | 5.4 | 6.1 | 5.8 |
| 10 | 62.6 | 62.2 | 4.6 | 4.5 | 17.2 | 17.2 |
| 11 | 66.3 | 66.1 | 5.2 | 5.2 | 18.2 | 17.9 |
| 12 | 62.6 | 62.3 | 4.6 | 4.7 | 17.2 | 16.8 |
| 13 | 49.7 | 50.0 | 4.2 | 4.0 | 17.8 | 17.7 |
| 14 | 63.8 | 64.0 | 7.0 | 6.9 | 18.6 | 18.4 |
| 15 | 70.0 | 69.7 | 6.7 | 6.7 | 18.6 | 18.5 |
| 16 | 62.7 | 62.6 | 6.7 | 6.9 | 18.8 | 18.9 |
| 17 | 61.3 | 61.2 | 4.9 | 4.5 | 15.1 | 15.0 |
| 18 | 67.8 | 67.7 | 6.0 | 6.0 | 16.7 | 16.5 |
| 19 | 52.6 | 53.1 | 5.0 | 5.4 | 16.4 | 16.0 |
| 20 | 60.3 | 60.3 | 4.5 | 4.6 | 15.6 | 15.6 |
| 21 | 51.2 | 51.0 | 4.6 | 4.9 | 17.0 | 16.6 |
| 22 | 67.1 | 66.6 | 5.6 | 5.5 | 17.4 | 16.9 |
| 23 | 62.9 | 62.9 | 6.3 | 6.4 | 19.6 | 19.4 |
| 24 | 63.5 | 63.6 | 5.0 | 5.0 | 16.5 | 16.3 |
| 25 | 62.5 | 62.4 | 7.0 | 7.1 | 19.4 | 19.1 |
| 26 | 61.3 | 61.3 | 6.6 | 6.6 | 20.4 | 19.8 |
| 27 | 64.0 | 63.8 | 6.7 | 6.6 | 18.6 | 18.2 |
| 28 | 64.4 | 64.4 | 5.4 | 5.4 | 15.8 | 15.8 |
| 29 | 61.3 | 61.4 | 4.9 | 4.8 | 15.0 | 15.0 |
| 30 | 67.8 | 67.9 | 6.0 | 6.1 | 16.7 | 16.6 |
| 31 | 64.0 | 63.7 | 6.7 | 6.6 | 18.6 | 18.5 |
| 32 | 63.6 | 63.0 | 7.3 | 7.2 | 18.5 | 18.6 |
| 33 | 62.5 | 62.2 | 7.0 | 6.6 | 19.4 | 18.9 |
| 34 | 52.6 | 53.0 | 5.0 | 5.6 | 16.4 | 16.7 |
| 35 | 64.9 | 64.8 | 7.0 | 7.1 | 17.8 | 17.5 |

TABLE IX-continued

| | Analysis (%) | | | | | |
|---|---|---|---|---|---|---|
| Ex. | C | | H | | N | |
| No. | Calc. | Found | Calc. | Found | Calc. | Found |
| 36 | 64.9 | 64.9 | 7.0 | 6.9 | 17.8 | 17.6 |
| 37 | 64.8 | 64.4 | 4.9 | 4.8 | 15.9 | 15.5 |
| 38 | 69.2 | 69.7 | 6.6 | 6.7 | 15.4 | 15.4 |
| 39 | 68.4 | 68.4 | 6.6 | 6.3 | 15.9 | 15.9 |
| 40 | 69.2 | 68.9 | 6.6 | 6.2 | 15.4 | 15.3 |
| 41 | 61.7 | 62.0 | 4.7 | 4.9 | 26.1 | 26.5 |
| 42 | 49.3 | 49.0 | 2.6 | 2.6 | 20.9 | 20.8 |
| 43 | 69.6 | 70.0 | 4.4 | 4.5 | 20.3 | 20.3 |
| 44 | 61.8 | 62.3 | 3.6 | 3.3 | 18.0 | 18.1 |
| 45 | 64.4 | 64.0 | 5.8 | 5.6 | 23.1 | 23.2 |
| 46 | 65.6 | 65.5 | 6.3 | 6.2 | 21.9 | 21.9 |
| 47 | 69.6 | 69.4 | 4.4 | 4.4 | 20.3 | 20.0 |
| 48 | 74.5 | 74.2 | 4.2 | 4.2 | 16.6 | 16.4 |
| 49 | 58.2 | 58.2 | 2.7 | 2.8 | 17.0 | 16.7 |
| 50 | 70.2 | 70.3 | 5.0 | 4.9 | 19.0 | 19.3 |
| 51 | 63.2 | 63.0 | 5.3 | 5.6 | 25.5 | 25.4 |
| 52 | 51.1 | 50.9 | 3.2 | 3.6 | 19.8 | 19.4 |
| 53 | 56.6 | 56.1 | 4.7 | 4.4 | 18.0 | 17.8 |
| 54 | 46.0 | 46.2 | 2.8 | 2.7 | 14.6 | 14.6 |
| 55 | 65.1 | 64.7 | 4.5 | 5.0 | 14.2 | 14.4 |
| 56 | 65.1 | 64.7 | 4.4 | 4.6 | 14.2 | 13.9 |
| 57 | 66.0 | 66.0 | 4.9 | 4.9 | 13.6 | 13.6 |
| 58 | 61.1 | 61.0 | 6.2 | 6.2 | 15.3 | 15.4 |
| 59 | 48.0 | 47.6 | 3.4 | 3.2 | 14.0 | 13.8 |
| 60 | 53.7 | 53.4 | 3.2 | 3.0 | 14.7 | 14.8 |
| 61 | 76.3 | 76.0 | 5.1 | 5.2 | 11.8 | 11.7 |
| 62 | 56.4 | 56.2 | 3.6 | 3.9 | 15.5 | 15.6 |
| 63 | 53.7 | 54.0 | 3.2 | 3.4 | 14.7 | 14.8 |
| 64 | 51.5 | 52.0 | 4.0 | 4.2 | 17.2 | 17.1 |
| 65 | 42.4 | 42.8 | 2.7 | 2.9 | 15.2 | 15.3 |
| 66 | 51.3 | 50.9 | 2.8 | 2.9 | 14.1 | 14.0 |
| 67 | 51.2 | 50.8 | 4.6 | 4.7 | 17.1 | 17.0 |
| 68 | 51.2 | 51.0 | 4.6 | 4.8 | 17.1 | 17.2 |
| 69 | 52.6 | 52.6 | 5.0 | 5.1 | 16.4 | 16.2 |
| 70 | 52.6 | 52.7 | 5.0 | 5.1 | 16.4 | 16.3 |
| 71 | 44.8 | 44.8 | 3.5 | 3.5 | 16.1 | 15.8 |
| 72 | 48.1 | 47.2 | 3.1 | 3.3 | 21.5 | 21.0 |
| 73 | 54.2 | 54.0 | 4.8 | 4.8 | 15.8 | 15.6 |
| 74 | 48.8 | 48.8 | 4.4 | 4.3 | 16.3 | 16.1 |
| 75 | 54.5 | 54.1 | 4.3 | 4.3 | 15.9 | 15.2 |
| 76 | 48.1 | 48.1 | 3.7 | 3.7 | 18.7 | 18.5 |
| 77 | 44.1 | 43.9 | 3.0 | 3.3 | 13.8 | 13.6 |
| 78 | 51.9 | 51.8 | 3.4 | 3.5 | 17.3 | 17.1 |
| 79 | 48.7 | 48.9 | 4.2 | 4.1 | 17.8 | 17.8 |
| 80 | 66.4 | 66.8 | 4.9 | 4.6 | 15.1 | 14.0 |
| 81 | 65.0 | 64.8 | 4.0 | 4.1 | 13.8 | 13.7 |
| 82 | 68.3 | 68.3 | 5.4 | 5.3 | 16.8 | 16.4 |
| 83 | 52.6 | 52.6 | 5.0 | 5.1 | 16.4 | 16.2 |
| 84 | 53.9 | 53.5 | 5.4 | 5.4 | 15.7 | 15.1 |
| 85 | 51.3 | 51.2 | 2.8 | 2.9 | 14.1 | 13.9 |
| 86 | 49.1 | 49.4 | 5.0 | 5.0 | 16.3 | 16.6 |
| 87 | 53.9 | 54.1 | 5.4 | 5.4 | 15.7 | 15.5 |
| 88 | 56.9 | 57.3 | 5.4 | 5.5 | 15.7 | 15.8 |
| 89 | 67.5 | 67.7 | 6.3 | 6.4 | 16.0 | 15.9 |
| 90 | 67.8 | 67.9 | 6.0 | 6.1 | 16.7 | 16.6 |
| 91 | 57.4 | 57.3 | 4.0 | 4.0 | 14.9 | 15.0 |
| 92 | 65.2 | 65.4 | 5.7 | 5.8 | 15.2 | 15.4 |
| 93 | 64.4 | 64.8 | 5.4 | 5.8 | 15.8 | 15.9 |
| 94 | 63.5 | 63.2 | 5.0 | 5.1 | 16.5 | 16.3 |
| 95 | 62.9 | 62.7 | 6.3 | 6.1 | 19.6 | 19.5 |
| 96 | 62.6 | 62.8 | 4.6 | 4.7 | 17.2 | 17.1 |
| 97 | 54.8 | 54.8 | 3.6 | 3.9 | 14.2 | 13.9 |
| 98 | 57.4 | 57.4 | 4.0 | 4.2 | 14.9 | 14.7 |
| 99 | 52.9 | 52.9 | 4.4 | 4.9 | 16.5 | 16.1 |
| 100 | 53.9 | 53.7 | 5.4 | 5.1 | 15.7 | 15.6 |
| 101 | 52.9 | 52.5 | 4.4 | 5.0 | 16.5 | 16.4 |
| 102 | 54.2 | 54.2 | 4.8 | 4.7 | 15.8 | 15.8 |
| 103 | 52.9 | 52.6 | 4.4 | 4.4 | 16.5 | 16.5 |
| 104 | 52.9 | 52.8 | 4.4 | 4.3 | 16.5 | 16.5 |
| 105 | 64.9 | 64.5 | 7.0 | 7.2 | 17.8 | 17.6 |
| 106 | 64.7 | 64.6 | 7.4 | 7.6 | 17.8 | 17.6 |
| 107 | 63.8 | 63.8 | 7.0 | 6.7 | 18.6 | 18.4 |
| 108 | 68.5 | 68.9 | 6.3 | 6.3 | 16.0 | 16.4 |

TABLE IX-continued

| Ex. No. | Analysis (%) | | | | | |
|---|---|---|---|---|---|---|
| | C | | H | | N | |
| | Calc. | Found | Calc. | Found | Calc. | Found |
| 109 | 62.2 | 61.8 | 5.2 | 5.1 | 14.5 | 14.4 |
| 110 | 49.7 | 49.4 | 4.2 | 4.1 | 17.8 | 17.3 |
| 111 | 52.3 | 52.7 | 5.0 | 5.1 | 16.3 | 16.3 |
| 112 | 51.0 | 51.0 | 3.6 | 4.2 | 15.9 | 16.0 |
| 113 | 56.5 | 56.2 | 5.5 | 5.4 | 14.6 | 14.5 |
| 114 | 69.8 | 69.6 | 6.9 | 6.8 | 14.8 | 14.7 |
| 115 | 62.5 | 62.1 | 4.6 | 4.4 | 17.2 | 17.1 |
| 116 | 51.5 | 51.4 | 4.0 | 4.1 | 17.2 | 17.0 |
| 117 | 61.8 | 61.9 | 5.9 | 5.9 | 20.6 | 20.7 |
| 118 | 59.3 | 59.1 | 4.1 | 4.0 | 16.3 | 16.0 |
| 119 | 68.0 | 68.3 | 4.4 | 4.6 | 14.4 | 14.3 |
| 120 | 68.0 | 68.0 | 4.4 | 4.5 | 14.4 | 14.4 |
| 121 | 61.7 | 61.5 | 5.9 | 5.9 | 20.6 | 20.4 |
| 122 | 62.5 | 62.0 | 7.0 | 7.2 | 19.4 | 19.3 |
| 123 | 67.8 | 67.4 | 6.0 | 6.1 | 16.7 | 16.2 |
| 124 | 71.8 | 71.8 | 5.2 | 5.3 | 14.6 | 14.5 |
| 125 | 68.6 | 68.2 | 4.8 | 4.9 | 13.9 | 13.5 |
| 126 | 68.2 | 68.0 | 5.4 | 5.7 | 15.8 | 15.9 |
| 127 | 54.8 | 54.9 | 3.6 | 3.4 | 14.2 | 14.2 |
| 128 | 52.9 | 52.5 | 4.4 | 4.1 | 16.5 | 16.4 |
| 129 | 54.2 | 54.0 | 4.8 | 5.0 | 15.8 | 15.6 |
| 130 | 67.1 | 66.7 | 5.6 | 5.4 | 17.4 | 17.1 |
| 131 | 63.5 | 63.5 | 5.0 | 4.9 | 16.5 | 16.6 |
| 132 | 63.5 | 63.3 | 5.0 | 4.8 | 16.5 | 16.0 |
| 133 | 62.9 | 62.8 | 6.3 | 6.2 | 19.6 | 19.3 |
| 134 | 60.3 | 59.9 | 4.5 | 4.7 | 15.6 | 15.5 |
| 135 | 52.5 | 52.2 | 4.5 | 4.8 | 13.1 | 13.2 |
| 136 | 55.9 | 56.5 | 4.0 | 4.3 | 13.7 | 13.8 |
| 137 | 57.5 | 58.0 | 4.0 | 4.2 | 14.9 | 14.9 |
| 138 | 58.6 | 59.2 | 4.4 | 4.6 | 14.4 | 14.5 |
| 139 | 54.8 | 54.9 | 3.6 | 3.7 | 14.2 | 14.2 |
| 140 | 52.9 | 52.6 | 4.4 | 4.4 | 16.5 | 16.4 |
| 141 | 44.0 | 44.1 | 3.2 | 3.2 | 14.7 | 14.6 |
| 142 | 45.5 | 45.2 | 3.6 | 3.5 | 14.1 | 14.2 |
| 143 | 52.4 | 52.6 | 3.2 | 3.4 | 13.6 | 13.3 |
| 144 | 52.6 | 52.5 | 5.0 | 5.4 | 16.4 | 16.7 |
| 145 | 53.9 | 53.7 | 5.4 | 5.3 | 15.7 | 15.7 |
| 146 | 52.6 | 52.2 | 5.0 | 5.5 | 16.4 | 16.1 |
| 147 | 53.9 | 54.3 | 5.4 | 5.6 | 15.7 | 15.4 |
| 148 | 54.0 | 53.7 | 5.4 | 5.8 | 15.7 | 15.4 |
| 149 | 55.1 | 55.4 | 5.7 | 6.2 | 15.1 | 15.1 |
| 150 | 53.9 | 54.2 | 5.4 | 5.5 | 15.7 | 15.6 |
| 151 | 55.1 | 55.5 | 5.7 | 5.7 | 15.1 | 15.2 |
| 152 | 69.2 | 68.8 | 5.1 | 5.2 | 13.4 | 13.0 |
| 153 | 66.3 | 65.9 | 4.6 | 4.9 | 12.9 | 12.8 |
| 154 | 69.2 | 68.7 | 5.1 | 5.2 | 13.4 | 13.3 |
| 155 | 71.9 | 71.7 | 5.2 | 5.6 | 14.6 | 14.3 |
| 156 | 63.5 | 63.4 | 7.3 | 7.2 | 18.5 | 18.1 |
| 157 | 55.1 | 55.1 | 5.7 | 5.6 | 15.1 | 15.0 |
| 158 | 50.8 | 51.0 | 4.6 | 4.8 | 16.9 | 16.7 |
| 159 | 45.5 | 45.0 | 3.3 | 3.5 | 13.3 | 13.3 |
| 160 | 53.4 | 53.3 | 5.0 | 5.5 | 14.6 | 14.7 |
| 161 | 58.5 | 58.7 | 4.4 | 4.4 | 14.3 | 14.4 |
| 162 | 71.9 | 72.2 | 5.2 | 5.4 | 14.6 | 14.4 |
| 163 | 72.3 | 72.5 | 5.6 | 5.6 | 14.1 | 13.9 |
| 164 | 65.8 | 65.4 | 6.3 | 6.6 | 14.6 | 14.3 |
| 165 | 65.2 | 65.0 | 5.7 | 6.0 | 15.2 | 14.9 |
| 166 | 64.4 | 64.0 | 5.4 | 5.3 | 15.8 | 15.9 |
| 167 | 65.2 | 65.5 | 5.7 | 6.0 | 15.2 | 15.0 |
| 168 | 53.9 | 53.7 | 4.3 | 4.0 | 13.9 | 13.8 |
| 169 | 59.7 | 59.4 | 4.3 | 4.2 | 13.9 | 13.6 |
| 170 | 54.1 | 54.1 | 3.7 | 3.8 | 18.6 | 18.2 |
| 171 | 47.4 | 47.0 | 4.3 | 4.6 | 21.3 | 21.4 |
| 172 | 40.7 | 40.3 | 2.9 | 2.9 | 18.3 | 18.2 |
| 173 | 51.6 | 51.0 | 3.3 | 3.3 | 17.7 | 17.4 |
| 174 | 64.1 | 64.1 | 5.7 | 5.8 | 20.8 | 21.0 |
| 175 | 65.7 | 65.5 | 6.3 | 6.4 | 19.1 | 18.7 |
| 176 | 54.8 | 54.8 | 3.6 | 3.5 | 14.2 | 14.0 |
| 177 | 52.9 | 52.6 | 4.4 | 4.2 | 16.5 | 16.6 |

EXAMPLE 178

Herbicidal Activity

To evaluate their herbicidal activity, compounds according to the invention were tested using a representative range of plants: maize, *Zea mays* (Mz); rice, *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB); and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam. The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0-9 scale. A rating 0 indicates growth as untreated control, a rating 9 indicates death. An increase of 1 unit on the linear scale approximates to a 10% increase in the level of effect.

The results of the tests are set out in Table XII below, in which the compounds are identified by reference to the preceding Examples. Absence of a numeral in the Table indicates a zero rating; an asterisk indicates that no result was obtained.

TABLE XII

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 10 | 7 | 7 | 6 | 6 | 5 | 6 | 9 | 3 | 5 | 7 | 5 | 9 | 4 | 8 | 8 | 9 | 7 | 5 | 4 | 9 | 7 | 8 | 9 | 8 | 4 |
|  |  |  |  |  |  |  |  |  | 1 | 5 | 2 | 7 | 3 | 7 | 7 | 9 | 6 | 2 | 3 | 8 | 5 | 6 | 9 | 7 | 2 |
| 11 | 7 | 6 | 5 | 4 | 4 | 6 | 3 | 2 | 5 | 7 | 5 | 7 | 5 | 7 | 9 | 9 | 8 | 7 | 7 | 6 | 4 | 3 | 7 | 7 | 2 |
|  |  |  |  |  |  |  |  |  | 1 | 4 | 3 | 5 | 3 | 7 | 8 | 9 | 7 | 6 | 6 | 6 | 2 | 2 | 5 | 3 |  |
| 12 | 5 | 2 | 5 | 4 | 2 | 3 | 7 |  | 5 | 7 | 5 | 7 | 4 | 6 | 8 | 9 | 7 |  |  |  |  | 1 | 2 |  |  |
|  |  |  |  |  |  |  |  |  | 1 | 5 | 3 | 5 | 3 | 6 | 8 | 9 | 6 |  |  |  |  | 1 | 1 |  |  |
| 13 | 7 | 4 | 7 | 3 | 6 | 7 | 9 | 7 | 5 | 3 | 2 | 7 | 3 | 7 | 9 | 8 | 7 | 9 | 3 | 9 | 3 | 6 | 9 | 9 | 7 |
|  |  |  |  |  |  |  |  |  | 1 | 2 |  | 2 |  | 5 | 8 | 8 | 6 | 2 |  | 6 |  | 4 | 8 | 8 | 6 |
| 23 | 7 | 7 | 7 | 6 | 7 | 8 | 9 | 8 | 5 | 4 |  | 8 | 5 | 6 | 9 | 9 | 7 | 8 | 7 | 8 | 7 | 8 | 7 | 9 | 8 |
|  |  |  |  |  |  |  |  |  | 1 | 2 |  | 7 | 4 | 5 | 8 | 9 | 6 | 8 | 4 | 8 | 4 | 5 | 4 | 5 | 4 |
| 24 | 6 | 5 | 7 | 6 | 4 | 8 | 9 | 2 | 5 | 6 |  | 7 | 5 | 9 | 9 | 9 | 7 | 5 | 2 | 9 | 6 | 7 | 9 | 9 | 6 |
|  |  |  |  |  |  |  |  |  | 1 | 2 |  | 7 | 2 | 8 | 8 | 9 | 6 | 4 |  | 8 | 2 | 5 | 9 | 8 | 2 |
| 25 | 8 | 7 | 5 | 4 | 6 | 9 | 8 | 8 | 5 | 5 | 2 | 8 | 3 | 5 | 9 | 8 | 8 | 7 | 4 | 8 | 4 | 5 | 8 | 9 | 7 |
|  |  |  |  |  |  |  |  |  | 1 | 2 |  | 6 |  | 4 | 7 | 7 | 8 | 5 |  | 5 |  | 3 | 2 | 8 | 2 |
| 26 | 8 | 4 | 8 | 5 | 6 | 8 | 8 | 8 | 5 | 3 | 2 | 8 | 4 | 5 | 8 | 8 | 8 | 8 | 6 | 8 | 8 | 4 | 6 | 8 | 4 |
|  |  |  |  |  |  |  |  |  | 1 | 1 |  | 5 |  | 3 | 6 | 6 | 7 | 5 | 2 | 8 | 7 | 2 | 5 | 8 | 2 |
| 27 | 6 | 4 | 5 | 4 | 3 | 6 | 7 | 6 | 5 | 4 |  | 8 | 2 | 5 | 8 | 7 | 7 | 8 | 2 | 8 | 4 |  | 3 | 5 | 2 |
|  |  |  |  |  |  |  |  |  | 1 | 3 |  | 3 | 2 | 4 | 6 | 7 | 6 | 2 |  | 6 |  |  |  |  |  |
| 28 | 5 | 2 | 7 | 4 | 4 | 7 | 8 | 1 | 5 | 6 | 4 | 9 | 6 | 8 | 9 | 9 | 8 | 5 | 2 | 9 | 7 | 7 | 9 | 8 | 2 |
|  |  |  |  |  |  |  |  |  | 1 | 5 | 4 | 8 | 5 | 8 | 9 | 9 | 8 | 4 |  | 8 | 6 | 5 | 9 | 8 |  |
| 29 | 4 | 4 | 7 | 5 | 2 | 5 | 6 | 1 | 5 | 7 | 5 | 9 | 6 | 7 | 9 | 9 | 7 | 4 |  | 8 | 7 | 4 | 9 | 9 | 2 |
|  |  |  |  |  |  |  |  |  | 1 | 6 | 3 | 8 | 5 | 7 | 9 | 9 | 7 | 4 |  | 8 | 6 | 4 | 9 | 9 |  |
| 30 | 5 | 5 | 7 | 7 | 3 | 7 | 7 | 1 | 5 | 6 | 1 | 8 | 5 | 8 | 9 | 9 | 7 | 4 |  | 9 | 6 | 8 | 9 | 9 | 2 |
|  |  |  |  |  |  |  |  |  | 1 | 5 |  | 7 | 5 | 7 | 9 | 9 | 7 | 4 |  | 8 | 5 | 4 | 9 | 8 |  |
| 31 | 8 | 6 | 8 | 5 | 8 | 9 | 8 | 8 | 5 | 7 | 4 | 9 | 3 | 8 | 8 | 9 | 8 | 8 | 4 | 8 | 7 | 5 | 8 | 9 | 4 |
|  |  |  |  |  |  |  |  |  | 1 | 5 |  | 8 | 3 | 7 | 8 | 9 | 8 | 7 | 2 | 7 | 6 | 4 | 6 | 8 | 2 |
| 32 | 8 | 5 | 8 | 7 | 6 | 8 | 8 | 7 | 5 | 6 | 4 | 9 | 4 | 7 | 9 | 9 | 8 | 7 | 4 | 8 | 3 | 2 | 7 | 9 | 2 |
|  |  |  |  |  |  |  |  |  | 1 | 5 | 4 | 7 | 3 | 5 | 9 | 8 | 6 | 6 |  | 6 |  |  | 2 | 5 |  |
| 33 | 8 | 7 | 8 | 7 | 5 | 8 | 9 | 8 | 5 | 7 |  | 9 | 5 | 8 | 9 | 8 | 8 | 7 | 5 | 9 | 4 |  |  |  |  |
|  |  |  |  |  |  |  |  |  | 1 | 2 |  | 5 | 2 | 6 | 7 | 7 | 8 | 6 | 4 | 8 |  |  |  |  |  |
| 34 | 8 | 7 | 8 | 8 | 4 | 8 | 9 | 8 | 5 | 7 | 2 | 9 | 5 | 8 | 9 | 9 | 9 | 8 | 6 | 9 | 7 | 8 | 9 | 8 | 6 |
|  |  |  |  |  |  |  |  |  | 1 | 5 |  | 8 | 3 | 6 | 8 | 9 | 7 | 7 | 5 | 8 | 5 | 2 | 8 | 8 | 2 |
| 35 | 6 | 3 | 7 | 2 | 3 | 7 | 4 | 5 | 5 | 6 | 2 | 9 | 4 | 6 | 9 | 8 | 7 | 7 | 2 | 8 | 1 |  | 8 | 2 | 1 |
|  |  |  |  |  |  |  |  |  | 1 | 4 |  | 6 | 2 | 5 | 8 | 7 | 6 | 2 |  | 5 |  |  | 2 |  |  |
| 36 | 4 |  | 5 |  |  | 2 |  | 3 | 5 | 5 |  | 8 | 3 | 5 | 8 | 7 | 7 | 4 |  | 8 |  |  | 2 | 5 | 2 | 1 |
|  |  |  |  |  |  |  |  |  | 1 | 3 |  | 4 | 3 | 2 | 4 | 6 | 5 |  |  | 2 |  |  |  |  |  |
| 37 | 6 | 5 | 8 | 7 | 3 | 5 | 6 | 2 | 5 | 5 |  | 8 | 6 | 8 | 9 | 9 | 7 | 5 |  | 7 | 4 | 6 | 9 | 9 | 4 |
|  |  |  |  |  |  |  |  |  | 1 | 4 |  | 7 | 5 | 8 | 8 | 9 | 6 | 2 |  | 5 | 2 | 5 | 9 | 8 | 2 |
| 39 | 6 | 2 | 8 | 6 | 7 | 8 | 8 | 5 | 5 | 5 | 3 | 9 | 6 | 8 | 9 | 9 | 8 | 6 | 2 | 8 | 7 | 6 | 9 | 8 | 3 |
|  |  |  |  |  |  |  |  |  | 1 | 4 |  | 6 | 3 | 7 | 8 | 8 | 8 | 4 |  | 6 | 5 | 6 | 7 | 6 |  |
| 41 |  |  |  |  |  |  |  |  | 5 | 3 |  | 6 |  | 2 | 6 | 6 | 6 |  |  |  |  |  |  |  |  |
|  |  |  |  |  |  |  |  |  | 1 |  |  | 5 |  |  | 6 | 5 | 4 |  |  |  |  |  |  |  |  |
| 42 | 4 |  | 3 | 2 | 4 | 3 | 5 | 6 | 5 | 4 |  | 6 | 4 | 5 | 7 | 8 | 8 | 6 |  | 8 | 4 | 5 | 8 | 9 | 4 |
|  |  |  |  |  |  |  |  |  | 1 | 2 |  | 5 | 2 | 4 | 6 | 8 | 7 | 5 |  | 7 |  | 2 | 7 | 6 |  |
| 43 | 3 | 2 | 3 |  |  | 2 | 3 |  | 5 | 3 |  | 5 | 4 | 5 | 7 | 9 | 6 |  |  | 2 |  | 3 | 2 | 2 |  |
|  |  |  |  |  |  |  |  |  | 1 | 2 |  | 2 |  | 4 | 5 | 7 | 5 |  |  |  |  |  |  |  |  |
| 44 |  |  |  |  |  |  |  |  | 5 |  |  |  |  | 2 | 7 | 5 | 4 |  |  |  |  |  |  |  |  |
|  |  |  |  |  |  |  |  |  | 1 |  |  |  |  | 1 | 6 | 2 | 2 |  |  |  |  |  |  |  |  |
| 45 |  |  |  |  |  |  |  |  | 5 | 2 |  | 3 | 2 | 4 | 5 | 6 | 7 |  |  |  |  |  |  |  |  |
|  |  |  |  |  |  |  |  |  | 1 |  |  | 2 |  | 2 | 4 | 2 | 5 |  |  |  |  |  |  |  |  |
| 46 | 4 |  | 5 |  | 4 | 5 | 4 | 3 | 5 | 3 |  | 6 | 3 | 6 | 7 | 8 | 8 | 4 |  | 6 |  | 4 | 7 | 9 | 6 |
|  |  |  |  |  |  |  |  |  | 1 |  |  | 2 |  | 5 | 6 | 7 | 7 |  |  | 2 |  |  | 5 | 4 | 2 |
| 47 |  |  |  |  |  |  |  |  | 5 | 3 |  | 2 |  | 4 | 7 | 9 | 4 |  |  |  |  |  |  |  |  |
|  |  |  |  |  |  |  |  |  | 1 |  |  |  | 2 | 5 | 5 | 7 | 2 |  |  |  |  |  |  |  |  |
| 48 |  |  |  |  |  |  |  |  | 5 | 4 |  | 4 | 3 | 5 | 7 | 8 | 5 |  |  |  |  |  | 2 | 2 |  |
|  |  |  |  |  |  |  |  |  | 1 | 3 |  | 2 | 2 | 4 | 7 | 6 | 4 |  |  |  |  |  |  |  |  |
| 49 |  |  |  |  |  |  |  |  | 5 | 2 |  | 2 |  | 3 | 8 | 4 | 3 |  |  |  |  |  |  |  |  |
|  |  |  |  |  |  |  |  |  | 1 |  |  |  |  |  | 7 | 2 |  |  |  |  |  |  |  |  |  |
| 60 | 5 | 4 | 5 | 6 | 2 | 5 | 5 |  | 5 | 5 | 4 | 8 | 7 | 6 | 8 | 9 | 8 | 5 |  | 7 | 5 | 3 | 8 | 9 | 3 |
|  |  |  |  |  |  |  |  |  | 1 | 3 | 1 | 8 | 5 | 5 | 8 | 9 | 7 | 2 |  | 6 | 5 | 2 | 7 | 9 | 2 |
| 61 | 1 | 1 | 3 | 4 |  | 2 | 7 | 1 | 5 | 5 | 4 | 8 | 6 | 5 | 8 | 9 | 8 | 2 |  | 3 | 1 | 2 | 8 | 8 | 4 |
|  |  |  |  |  |  |  |  |  | 1 | 4 | 4 | 6 | 5 | 5 | 8 | 9 | 7 | 2 |  | 1 | 1 | 2 | 8 | 8 |  |
| 62 | 4 | 3 | 7 | 6 | 2 | 5 | 6 |  | 5 | 6 | 5 | 9 | 8 | 9 | 9 | 9 | 8 | 4 | 3 | 8 | 6 | 5 | 9 | 9 | 4 |
|  |  |  |  |  |  |  |  |  | 1 | 5 | 2 | 9 | 7 | 8 | 9 | 9 | 7 | 2 | 2 | 7 | 4 | 5 | 8 | 8 | 2 |
| 63 | 4 | 2 | 7 | 7 | 3 | 3 | 6 | 2 | 5 | 7 | 4 | 9 | 6 | 8 | 9 | 9 | 7 | 4 | 3 | 6 | 4 | 7 | 9 | 9 | 6 |
|  |  |  |  |  |  |  |  |  | 1 | 5 |  | 8 | 5 | 7 | 9 | 9 | 6 | 2 |  | 5 | 2 | 6 | 9 | 8 | 5 |
| 64 | * | * | * | * | * | * | * | * | 5 | 8 | 6 | 9 | 8 | 8 | 9 | 9 | 8 | 8 | 8 | 9 | 9 | 9 | 9 | 9 | 9 |
|  |  |  |  |  |  |  |  |  | 1 | 8 | 2 | 9 | 6 | 8 | 9 | 9 | 8 | 7 | 7 | 9 | 8 | 7 | 9 | 9 | 5 |
| 65 | 7 | 6 | 8 | 7 | 5 | 8 | 9 | 7 | 5 | 8 | 7 | 9 | 9 | 9 | 9 | 9 | 8 | 8 | 9 | 9 | 9 | 9 | 9 | 9 | 8 |
|  |  |  |  |  |  |  |  |  | 1 | 7 | 6 | 9 | 8 | 9 | 9 | 9 | 8 | 7 | 8 | 9 | 8 | 9 | 9 | 9 | 8 |
| 66 | 6 |  | 4 | 3 |  | 2 | 6 | 2 | 5 | 6 | 4 | 7 | 8 | 8 | 9 | 9 | 8 | 5 | 3 | 7 | 4 | 4 | 8 | 8 | 4 |
|  |  |  |  |  |  |  |  |  | 1 | 4 | 2 | 7 | 8 | 8 | 9 | 9 | 8 | 7 | 2 |  | 6 | 2 | 7 | 8 | 2 |
| 67 | 7 | 6 | 8 | 7 | 4 | 6 | 9 | 7 | 5 | 9 | 8 | 8 | 8 | 8 | 9 | 9 | 8 | 9 | 9 | 9 | 9 | 9 | 9 | 9 | 9 |
|  |  |  |  |  |  |  |  |  | 1 | 7 | 8 | 8 | 8 | 7 | 9 | 9 | 8 | 8 | 8 | 9 | 8 | 9 | 9 | 9 | 8 |

TABLE XII-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 68 | 7 | 7 | 8 | 7 | 4 | 6 | 4 | 6 | 5 | 8 | 8 | 8 | 8 | 8 | 9 | 9 | 8 | 9 | 9 | 9 | 9 | 9 | 9 | 9 | 9 |
| | | | | | | | | | 1 | 7 | 7 | 7 | 8 | 8 | 9 | 9 | 8 | 8 | 8 | 9 | 9 | 8 | 9 | 9 | 9 |
| 69 | 7 | 6 | 7 | 6 | 5 | 8 | 7 | 2 | 5 | 8 | 7 | 7 | 8 | 8 | 9 | 9 | 8 | 8 | 7 | 9 | 8 | 8 | 9 | 9 | 9 |
| | | | | | | | | | 1 | 7 | 6 | 7 | 8 | 8 | 9 | 9 | 8 | 8 | 7 | 8 | 8 | 8 | 9 | 9 | 8 |
| 70 | 7 | 2 | 7 | 6 | 5 | 7 | 5 | 6 | 5 | 8 | 8 | 9 | 9 | 8 | 9 | 9 | 8 | 9 | 8 | 9 | 8 | 9 | 9 | 9 | 9 |
| | | | | | | | | | 1 | 6 | 7 | 7 | 8 | 8 | 9 | 9 | 8 | 8 | 8 | 9 | 8 | 8 | 9 | 9 | 8 |
| 71 | 7 | 6 | 7 | 8 | 6 | 8 | 9 | 6 | 5 | 8 | 6 | 7 | 6 | 7 | 9 | 9 | 9 | 8 | 8 | 9 | 8 | 6 | 9 | 9 | 9 |
| | | | | | | | | | 1 | 6 | 5 | 6 | 5 | 6 | 8 | 9 | 8 | 7 | 7 | 9 | 7 | 2 | 8 | 9 | 4 |
| 72 | 6 | 5 | 7 | 6 | 2 | 7 | 6 | 7 | 5 | 4 | 4 | 6 | 2 | 6 | 8 | 8 | 9 | 8 | 4 | 6 | 4 | 5 | 6 | 9 | 7 |
| | | | | | | | | | 1 | 2 | | 5 | | 5 | 7 | 7 | 8 | 6 | | 5 | 3 | 4 | 5 | 8 | 2 |
| 73 | 8 | 4 | 6 | 7 | 6 | 7 | 9 | 5 | 5 | 8 | 6 | 8 | 5 | 7 | 8 | 8 | 9 | 8 | 8 | 9 | 8 | 7 | 9 | 9 | 9 |
| | | | | | | | | | 1 | 6 | 5 | 7 | 4 | 6 | 8 | 8 | 9 | 7 | 4 | 9 | 8 | 7 | 9 | 9 | 7 |
| 74 | 8 | 7 | 8 | 7 | 5 | 7 | 8 | 8 | 5 | 8 | 4 | 8 | 4 | 7 | 8 | 9 | 9 | 9 | 9 | 9 | 9 | 5 | 9 | 9 | 6 |
| | | | | | | | | | 1 | 5 | 2 | 7 | 2 | 7 | 8 | 8 | 9 | 8 | 8 | 8 | 7 | 4 | 9 | 9 | 5 |
| 75 | 7 | 6 | 8 | 7 | 6 | 7 | 8 | 6 | 5 | 7 | 6 | 8 | 7 | 8 | 9 | 9 | 9 | 8 | 6 | 9 | 8 | 6 | 9 | 9 | 7 |
| | | | | | | | | | 1 | 6 | 5 | 7 | 7 | 8 | 9 | 9 | 9 | 7 | 5 | 8 | 7 | 5 | 8 | 9 | 6 |
| 76 | 9 | 8 | 8 | 8 | 7 | 9 | 8 | 8 | 5 | 7 | 6 | 8 | 7 | 8 | 9 | 9 | 9 | 9 | 9 | 9 | 8 | 9 | 9 | 9 | 9 |
| | | | | | | | | | 1 | 4 | 5 | 7 | 6 | 7 | 9 | 9 | 8 | 9 | 8 | 9 | 8 | 7 | 9 | 9 | 8 |
| 77 | 6 | 6 | 7 | 7 | 6 | 6 | 4 | 2 | 5 | 8 | 6 | 8 | 8 | 9 | 9 | 9 | 9 | 6 | 4 | 8 | 7 | 6 | 9 | 9 | 5 |
| | | | | | | | | | 1 | 7 | 5 | 8 | 7 | 9 | 9 | 9 | 8 | 5 | 2 | 7 | 6 | 5 | 9 | 9 | 4 |
| 78 | 7 | 6 | 8 | 7 | 6 | 9 | 9 | 7 | 5 | 7 | 4 | 9 | 8 | 8 | 9 | 9 | 9 | 9 | 8 | 9 | 9 | 6 | 9 | 9 | 8 |
| | | | | | | | | | 1 | 6 | 2 | 8 | 7 | 8 | 9 | 9 | 8 | 7 | 6 | 8 | 7 | 5 | 8 | 8 | 7 |
| 79 | 8 | 8 | 9 | 8 | 7 | 9 | 9 | 8 | 5 | 9 | 7 | 9 | 8 | 9 | 9 | 9 | 9 | 9 | 9 | 9 | 9 | 9 | 9 | 9 | 9 |
| | | | | | | | | | 1 | 8 | 6 | 8 | 8 | 9 | 9 | 9 | 8 | 9 | 8 | 9 | 8 | 7 | 9 | 9 | 9 |
| 80 | | | | | | | | | 5 | 2 | | 3 | | 2 | 4 | 4 | 4 | | | | | | | | |
| | | | | | | | | | 1 | | | | | | 2 | 2 | 2 | | | | | | | | |
| 81 | | | 3 | 2 | 2 | 3 | 4 | | 5 | 6 | 4 | 7 | 4 | 6 | 8 | 9 | 7 | | | | | 2 | 4 | 7 | |
| | | | | | | | | | 1 | 5 | 2 | 6 | 2 | 5 | 8 | 9 | 7 | | | | | | 2 | 6 | |
| 82 | 7 | 6 | 7 | 6 | 4 | 7 | 6 | 4 | 5 | 4 | 2 | 7 | 5 | 6 | 9 | 9 | 8 | 4 | | 6 | 4 | 3 | 2 | 4 | |
| | | | | | | | | | 1 | 3 | | 7 | 4 | 6 | 8 | 9 | 8 | 2 | | 2 | 2 | | | 2 | |
| 83 | 7 | 7 | 6 | 5 | 6 | 9 | 8 | 2 | 5 | 8 | 8 | 9 | 8 | 7 | 9 | 9 | 9 | 7 | 8 | 9 | 9 | 9 | 9 | 9 | 9 |
| | | | | | | | | | 1 | 7 | 7 | 8 | 8 | 7 | 8 | 9 | 9 | 7 | 7 | 9 | 8 | 4 | 9 | 9 | 8 |
| 84 | 7 | 6 | 7 | 6 | 4 | 6 | 5 | 3 | 5 | 6 | 6 | 8 | 6 | 7 | 9 | 9 | 9 | 7 | 4 | 9 | 8 | 4 | 9 | 9 | 4 |
| | | | | | | | | | 1 | 5 | 4 | 7 | 6 | 7 | 9 | 9 | 9 | 6 | 2 | 8 | 7 | 2 | 7 | 8 | 2 |
| 85 | 6 | 3 | 5 | 7 | 2 | 4 | 7 | 2 | 5 | 7 | 4 | 7 | 6 | 4 | 9 | 9 | 9 | 3 | | 7 | 4 | 4 | 7 | 9 | 2 |
| | | | | | | | | | 1 | 2 | 2 | 7 | 5 | 4 | 9 | 9 | 8 | 2 | | 7 | 3 | 2 | 6 | 8 | |
| 86 | * | * | * | * | * | * | * | * | 5 | 8 | 6 | 8 | 8 | 8 | 9 | 9 | 9 | 9 | 8 | 9 | 9 | 9 | 9 | 9 | 9 |
| | | | | | | | | | 1 | 7 | 5 | 7 | 8 | 8 | 9 | 9 | 8 | 8 | 7 | 9 | 7 | 8 | 9 | 9 | 7 |
| 87 | 6 | 6 | 7 | 6 | 5 | 7 | 6 | 3 | 5 | 8 | 6 | 8 | 6 | 8 | 9 | 9 | 8 | 6 | 4 | 9 | 8 | 6 | 9 | 9 | 7 |
| | | | | | | | | | 1 | 4 | 2 | 7 | 5 | 8 | 9 | 9 | 8 | 2 | 2 | 9 | 7 | 5 | 9 | 9 | 4 |
| 88 | 7 | 6 | 7 | 6 | 4 | 3 | 7 | 4 | 5 | 6 | 4 | 9 | 6 | 4 | 9 | 9 | 8 | 7 | 4 | 9 | 4 | 3 | 3 | 9 | 4 |
| | | | | | | | | | 1 | 5 | 2 | 6 | 5 | 2 | 8 | 8 | 7 | 2 | 2 | 8 | 2 | | 2 | 8 | 2 |
| 89 | 6 | | 4 | 3 | | 2 | | | 5 | 5 | | 8 | 6 | 5 | 8 | 9 | 7 | | | 4 | | 3 | 8 | 7 | |
| | | | | | | | | | 1 | 4 | | 2 | 5 | 5 | 8 | 9 | 7 | | | 2 | | | 7 | 7 | |
| 90 | 6 | | 5 | 6 | 4 | | 2 | | 5 | 6 | | 7 | 4 | 6 | 8 | 7 | 6 | 3 | | 4 | | | 6 | 4 | |
| | | | | | | | | | 1 | * | * | * | * | * | * | * | * | * | * | * | * | * | * | * | * |
| 91 | 4 | 6 | 7 | 6 | | 4 | 2 | | 5 | 4 | | 6 | 4 | 7 | 7 | 9 | 9 | 4 | 2 | 6 | | | 8 | 8 | 2 |
| | | | | | | | | | 1 | 2 | | 2 | 2 | 6 | 6 | 8 | 8 | 2 | | 5 | | | 7 | 7 | 8 |
| 92 | 6 | 4 | 5 | 2 | 2 | 6 | 5 | | 5 | 5 | 5 | 8 | 4 | 9 | 9 | 9 | 6 | 4 | 2 | 8 | 6 | 5 | 9 | 9 | 4 |
| | | | | | | | | | 1 | 4 | 2 | 8 | 2 | 7 | 9 | 9 | 5 | 2 | | 4 | 2 | 4 | 9 | 8 | 2 |
| 93 | 7 | 6 | 7 | 3 | 2 | 6 | 5 | | 5 | 7 | 2 | 8 | 6 | 9 | 9 | 9 | 7 | 5 | 2 | 7 | 6 | 7 | 9 | 9 | 2 |
| | | | | | | | | | 1 | 5 | 2 | 7 | 5 | 7 | 9 | 9 | 6 | 4 | | 5 | 5 | 6 | 8 | 8 | |
| 94 | | | | | | | | | 5 | | | 7 | | | 7 | 8 | 4 | | | | | | | | |
| | | | | | | | | | 1 | | | 2 | | | 5 | 2 | | | | | | | | | |
| 95 | | | | | | | | | 5 | 2 | | 3 | | 2 | 7 | 8 | 5 | | | | | | | | |
| | | | | | | | | | 1 | | | | | | 2 | 2 | 2 | | | | | | | | |
| 110 | 7 | 6 | 8 | 8 | 6 | 8 | 7 | 9 | 5 | 5 | | 8 | 4 | 6 | 9 | 9 | 9 | 9 | 8 | 9 | 9 | 5 | 9 | 9 | 9 |
| | | | | | | | | | 1 | 4 | | 6 | 3 | 5 | 9 | 9 | 8 | 8 | 6 | 2 | 8 | 4 | 6 | 8 | 2 |
| 111 | 7 | 6 | 8 | 8 | 6 | 9 | 9 | 9 | 5 | 7 | 7 | 8 | 6 | 7 | 9 | 9 | 9 | 9 | 9 | 9 | 9 | 6 | 9 | 9 | 8 |
| | | | | | | | | | 1 | 2 | 3 | 6 | 5 | 6 | 9 | 9 | 8 | 8 | 6 | 7 | 8 | 5 | 9 | 9 | 8 |
| 112 | | | 2 | | 3 | 5 | 4 | 3 | 5 | 4 | | 3 | 3 | 4 | 9 | 8 | 7 | 3 | | 4 | 3 | 2 | 4 | 9 | 3 |
| | | | | | | | | | 1 | 3 | | 1 | | 3 | 7 | 6 | 5 | | | 2 | | | 2 | 2 | |
| 115 | 5 | 6 | 6 | 5 | 5 | 6 | 7 | 4 | 5 | 7 | 4 | 8 | 6 | 7 | 9 | 9 | 7 | 4 | 5 | 7 | 4 | 3 | 9 | 7 | 4 |
| | | | | | | | | | 1 | 6 | 2 | 7 | 5 | 6 | 8 | 9 | 7 | 3 | 2 | 5 | 2 | 2 | 7 | 6 | 2 |
| 116 | 8 | 8 | 8 | 8 | 7 | 9 | 9 | 8 | 5 | 7 | 5 | 7 | 7 | 7 | 9 | 9 | 8 | 7 | 7 | 9 | 9 | 9 | 9 | 9 | 9 |
| | | | | | | | | | 1 | 6 | 4 | 7 | 6 | 7 | 8 | 8 | 8 | 7 | 7 | 9 | 8 | 8 | 9 | 9 | 8 |
| 117 | 7 | 4 | 6 | 3 | 5 | 6 | 8 | 7 | 5 | 7 | | 8 | 5 | 7 | 8 | 9 | 8 | 7 | 4 | 7 | 5 | 4 | 8 | 9 | 7 |
| | | | | | | | | | 1 | 2 | | 2 | 1 | 5 | 8 | 9 | 8 | | | 2 | | | 5 | 8 | 4 |
| 118 | 6 | 4 | 6 | 4 | 2 | 3 | 4 | | 5 | 6 | 5 | 8 | 6 | 5 | 9 | 9 | 4 | 2 | | 6 | 4 | 5 | 8 | 7 | |
| | | | | | | | | | 1 | 5 | 2 | 7 | 5 | 5 | 9 | 8 | 3 | | | 2 | | 4 | 8 | 6 | |
| 119 | 2 | | 7 | 5 | | 6 | 9 | 2 | 5 | 5 | | 8 | 6 | 6 | 9 | 9 | 6 | 4 | 6 | 4 | 6 | 7 | 9 | 4 | |
| | | | | | | | | | 1 | 4 | | 8 | 5 | 5 | 9 | 9 | 5 | 1 | 6 | 4 | 3 | 7 | 9 | 2 | |
| 120 | | | | | | | | | 5 | | | | | 2 | | 2 | | | | 5 | | 2 | 4 | | |
| | | | | | | | | | 1 | | | | | | | | | | | 2 | | | | | |

TABLE XII-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 121 | | | | | 3 | 4 | 3 | 2 | 5 | 3 | | 5 | 2 | 5 | 7 | 6 | 7 | 1 | | 3 | 2 | 1 | 3 | 4 | 1 |
| | | | | | | | | | 1 | 2 | | 4 | | 5 | 5 | 5 | 6 | | | | | | 2 | 2 | |
| 122 | 4 | 2 | 3 | 2 | 3 | 6 | 4 | 5 | 5 | 4 | 3 | 8 | 4 | 5 | 6 | 7 | 6 | 5 | 4 | 6 | | 4 | 7 | 9 | 6 |
| | | | | | | | | | 1 | 2 | | 2 | 2 | 4 | 5 | 6 | 5 | | | 2 | | | 2 | 2 | 2 |
| 123 | 4 | | 6 | 5 | 4 | 6 | 5 | | 5 | 6 | 4 | 9 | 4 | 7 | 8 | 9 | 8 | 5 | 2 | 7 | 2 | 3 | 6 | 6 | 4 |
| | | | | | | | | | 1 | 5 | 2 | 7 | 2 | 7 | 8 | 8 | 7 | 4 | | 2 | | 2 | 5 | 2 | 2 |
| 124 | 6 | | 6 | 3 | | 2 | 2 | | 5 | 2 | 1 | 6 | 4 | 6 | 8 | 7 | 6 | | | | | | 4 | 7 | |
| | | | | | | | | | 1 | | | 5 | 2 | 5 | 7 | 6 | 5 | | | | | | 2 | 6 | |
| 125 | | | | | | | | | 5 | 2 | | 6 | 4 | 4 | 8 | 9 | 6 | | | | | | 6 | 4 | |
| | | | | | | | | | 1 | 1 | | 5 | 2 | 2 | 7 | 6 | 6 | | | | | | 5 | 2 | |
| 126 | 4 | | 6 | | | 2 | 3 | | 5 | 6 | | 5 | 4 | 7 | 8 | 8 | 7 | 3 | | 4 | | 2 | 6 | 8 | |
| | | | | | | | | | 1 | 5 | | 4 | 2 | 5 | 7 | 7 | 6 | | | 2 | | | 6 | 7 | |
| 127 | * | * | * | * | * | * | * | * | 5 | 5 | 6 | 7 | 8 | 7 | 9 | 9 | 8 | 7 | 4 | 9 | 7 | 9 | 9 | 9 | 8 |
| | | | | | | | | | 1 | 2 | 2 | 7 | 8 | 7 | 8 | 7 | 8 | 5 | 2 | 8 | 5 | 8 | 8 | 9 | 4 |
| 128 | 8 | 8 | 7 | 7 | 4 | 9 | 9 | 8 | 5 | 5 | 4 | 9 | 7 | 7 | 7 | 9 | 8 | 7 | 7 | 9 | 9 | 9 | 9 | 9 | 9 |
| | | | | | | | | | 1 | 2 | 2 | 7 | 2 | 6 | 7 | 8 | 8 | 6 | 4 | 6 | 8 | 6 | 9 | 9 | 8 |
| 129 | 8 | 7 | 7 | 8 | 7 | 8 | 9 | 8 | 5 | 7 | 6 | 9 | 8 | 7 | 9 | 9 | 8 | 8 | 8 | 9 | 9 | 9 | 9 | 9 | 8 |
| | | | | | | | | | 1 | 5 | 2 | 8 | 7 | 7 | 9 | 9 | 8 | 7 | 7 | 9 | 9 | 8 | 9 | 9 | 8 |
| 130 | 5 | 4 | 2 | 6 | 6 | 7 | 5 | 6 | 5 | 4 | | 4 | 5 | 6 | 8 | 9 | 8 | 7 | 4 | 6 | 7 | 4 | 9 | 8 | 6 |
| | | | | | | | | | 1 | | | 2 | | 4 | 7 | 7 | 8 | 2 | | 2 | 5 | 2 | 8 | 7 | 4 |
| 131 | 5 | | 6 | 7 | 5 | 7 | 4 | 6 | 5 | 4 | 3 | 8 | 6 | 7 | 9 | 9 | 8 | 7 | 5 | 7 | 7 | 5 | 9 | 8 | 7 |
| | | | | | | | | | 1 | 2 | | 2 | 5 | 5 | 9 | 8 | 7 | 6 | 2 | 2 | 6 | 2 | 9 | 2 | 2 |
| 132 | 6 | 4 | 7 | 5 | 6 | 7 | 7 | 6 | 5 | 4 | | 7 | 5 | 7 | 8 | 9 | 8 | 7 | 5 | 7 | 8 | 5 | 9 | 9 | 6 |
| | | | | | | | | | 1 | 2 | | 2 | 4 | 6 | 8 | 7 | 7 | 6 | | 2 | 2 | 2 | 9 | 8 | 2 |
| 133 | | | | | 2 | 5 | 6 | 4 | 5 | 6 | | 4 | 3 | 2 | 7 | 9 | 8 | | | | | | 6 | 7 | 5 |
| | | | | | | | | | 1 | | | | | 1 | 6 | 6 | 6 | | | | | | 2 | 4 | 2 |
| 134 | 5 | | 4 | 3 | 2 | 7 | 2 | 5 | 5 | 5 | | 9 | 6 | 5 | 9 | 9 | 8 | 5 | | 7 | 2 | 1 | 9 | 8 | 5 |
| | | | | | | | | | 1 | 2 | | 7 | 2 | 4 | 9 | 8 | 6 | 2 | | 2 | | | 8 | 6 | 2 |
| 135 | 3 | | 5 | 4 | 6 | 4 | 6 | | 5 | 6 | 3 | 9 | 8 | 8 | 9 | 9 | 6 | 4 | 2 | 6 | 4 | 7 | 9 | 9 | 6 |
| | | | | | | | | | 1 | 4 | | 8 | 6 | 7 | 9 | 9 | 6 | 1 | | 5 | 2 | 6 | 8 | 9 | 2 |
| 136 | 5 | 6 | 7 | 5 | 3 | 6 | 7 | 4 | 5 | 6 | 5 | 9 | 7 | 7 | 9 | 9 | 8 | 5 | 4 | 6 | 4 | 6 | 9 | 9 | 6 |
| | | | | | | | | | 1 | 4 | 2 | 9 | 6 | 7 | 9 | 9 | 7 | 4 | 2 | 5 | 2 | 2 | 7 | 9 | 2 |
| 137 | 6 | 5 | 7 | 6 | 5 | 7 | 6 | 5 | 5 | 7 | 6 | 9 | 9 | 9 | 9 | 9 | 8 | 7 | 6 | 9 | 9 | 9 | 9 | 9 | 7 |
| | | | | | | | | | 1 | 6 | 5 | 8 | 8 | 9 | 9 | 9 | 8 | 6 | 5 | 8 | 8 | 8 | 9 | 9 | 7 |
| 138 | 4 | 3 | 4 | 6 | 5 | 6 | 7 | 5 | 5 | 7 | 6 | 9 | 8 | 9 | 9 | 9 | 7 | 6 | 6 | 8 | 8 | 9 | 9 | 9 | 6 |
| | | | | | | | | | 1 | 5 | 2 | 8 | 7 | 8 | 9 | 9 | 7 | 5 | 2 | 7 | 7 | 8 | 9 | 9 | 6 |
| 139 | 6 | 5 | 7 | 5 | 6 | 4 | 9 | 6 | 5 | 7 | 6 | 9 | 8 | 9 | 9 | 9 | 8 | 7 | 6 | 9 | 8 | 9 | 9 | 9 | 8 |
| | | | | | | | | | 1 | 5 | 2 | 9 | 7 | 8 | 9 | 9 | 7 | 6 | 4 | 9 | 7 | 8 | 9 | 9 | 6 |
| 140 | 5 | 4 | 6 | 8 | 4 | 6 | 7 | 8 | 5 | 5 | 3 | 9 | 5 | 8 | 9 | 9 | 8 | 8 | 7 | 9 | 9 | 7 | 9 | 9 | 7 |
| | | | | | | | | | 1 | 4 | | 6 | 4 | 7 | 9 | 9 | 8 | 6 | 4 | 8 | 6 | 4 | 8 | 9 | 6 |
| 141 | 4 | 6 | 7 | 7 | 4 | 7 | 9 | 6 | 5 | 5 | 4 | 7 | 6 | 7 | 9 | 9 | 8 | 7 | 5 | 9 | 8 | 6 | 9 | 9 | 7 |
| | | | | | | | | | 1 | 2 | 2 | 3 | 5 | 5 | 8 | 9 | 8 | 6 | 4 | 9 | 8 | 5 | 9 | 9 | 6 |
| 142 | 7 | 4 | 8 | 4 | 6 | 7 | 8 | 8 | 5 | 6 | 4 | 7 | 9 | 8 | 9 | 9 | 8 | 7 | 6 | 9 | 9 | 9 | 9 | 9 | 7 |
| | | | | | | | | | 1 | 4 | 2 | 7 | 8 | 8 | 9 | 9 | 8 | 5 | 5 | 8 | 7 | 6 | 9 | 9 | 6 |
| 143 | 4 | | 6 | 4 | 6 | 5 | 9 | 6 | 5 | 6 | 4 | 8 | 8 | 8 | 9 | 9 | 8 | 6 | 5 | 7 | 7 | 7 | 9 | 9 | 7 |
| | | | | | | | | | 1 | 5 | 3 | 7 | 7 | 8 | 9 | 9 | 7 | 6 | 4 | 7 | 6 | 7 | 9 | 9 | 6 |
| 144 | 4 | | 6 | 5 | | 4 | 8 | 6 | 5 | 5 | 3 | 9 | 7 | 8 | 9 | 9 | 8 | 9 | 8 | 9 | 8 | 6 | 9 | 9 | 8 |
| | | | | | | | | | 1 | 4 | | 7 | 7 | 7 | 9 | 9 | 8 | 8 | 6 | 7 | 8 | 5 | 9 | 9 | 7 |
| 145 | 7 | 5 | 7 | 7 | 5 | 6 | 9 | 6 | 5 | 7 | 8 | 9 | 8 | 8 | 9 | 9 | 8 | 9 | 8 | 9 | 9 | 8 | 9 | 9 | 9 |
| | | | | | | | | | 1 | 6 | 7 | 7 | 8 | 8 | 9 | 9 | 8 | 8 | 8 | 9 | 8 | 6 | 9 | 9 | 8 |
| 146 | 7 | | 6 | 8 | 4 | 7 | 7 | 8 | 5 | 5 | | 8 | 5 | 6 | 9 | 9 | 8 | 9 | 5 | 8 | 9 | 4 | 9 | 9 | 8 |
| | | | | | | | | | 1 | 2 | | 7 | 4 | 5 | 9 | 9 | 8 | 8 | 1 | 5 | 8 | 2 | 8 | 9 | 7 |
| 147 | 7 | 4 | 7 | 7 | 7 | 7 | 9 | 8 | 5 | 7 | 4 | 8 | 9 | 7 | 9 | 9 | 8 | 8 | 8 | 9 | 9 | 9 | 9 | 9 | 8 |
| | | | | | | | | | 1 | 2 | | 7 | 7 | 6 | 9 | 9 | 8 | 7 | 7 | 8 | 8 | 8 | 9 | 9 | 8 |
| 148 | 6 | 2 | 7 | 6 | 4 | 6 | 8 | 7 | 5 | 6 | 4 | 8 | 7 | 7 | 9 | 9 | 8 | 8 | 7 | 9 | 9 | 7 | 9 | 9 | 8 |
| | | | | | | | | | 1 | 2 | | 7 | 7 | 6 | 9 | 9 | 7 | 7 | 6 | 8 | 7 | 5 | 9 | 9 | 7 |
| 149 | 7 | 4 | 8 | 7 | 6 | 5 | 9 | 7 | 5 | 7 | 4 | 8 | 8 | 7 | 9 | 9 | 8 | 8 | 7 | 9 | 9 | 9 | 9 | 9 | 8 |
| | | | | | | | | | 1 | 6 | 2 | 7 | 8 | 7 | 9 | 9 | 8 | 7 | 6 | 9 | 8 | 7 | 9 | 9 | 6 |
| 150 | 4 | | 3 | | 2 | 5 | 7 | 6 | 5 | 5 | 3 | 9 | 6 | 5 | 9 | 9 | 8 | 5 | 2 | 3 | 8 | 4 | 9 | 9 | 6 |
| | | | | | | | | | 1 | 3 | | 2 | 2 | 2 | 7 | 8 | 8 | 2 | | 2 | 6 | 2 | 7 | 9 | 5 |
| 151 | 7 | 3 | 7 | 5 | 7 | 6 | 9 | 7 | 5 | 6 | 5 | 8 | 7 | 7 | 9 | 9 | 8 | 7 | 6 | 9 | 7 | 9 | 9 | 9 | 8 |
| | | | | | | | | | 1 | 4 | 1 | 6 | 3 | 7 | 9 | 9 | 8 | 6 | 2 | 7 | 6 | 8 | 9 | 9 | 7 |
| 152 | | | | | | | | | 5 | 3 | | 2 | 1 | 2 | 4 | 1 | 2 | | | | | | | | |
| | | | | | | | | | 1 | | | 1 | | 1 | 2 | | | | | | | | | | |
| 153 | | | | | | 2 | | | 5 | 4 | | 5 | | 4 | 8 | 6 | 6 | | | 2 | | 1 | 6 | | |
| | | | | | | | | | 1 | 2 | | 2 | | 2 | 4 | 4 | 2 | | | | | | 2 | | |
| 154 | * | * | * | * | * | * | * | * | 5 | | | | | 3 | 2 | 3 | 2 | | | | | | | | |
| | | | | | | | | | 1 | | | | | | 2 | | | | | | | | | | |
| 155 | | | | | | | | | 5 | | | | | | 4 | | 2 | | | | | | | | |
| | | | | | | | | | 1 | | | | | | 2 | | | | | | | | | | |
| 156 | | | | | | | | | 5 | 2 | | 6 | | 5 | 8 | 6 | 8 | | | | | | 3 | 2 | 1 |
| | | | | | | | | | 1 | | | 5 | | 2 | 6 | 6 | 7 | | | | | | | | |
| 157 | 8 | 6 | 7 | 7 | 6 | 8 | 9 | 8 | 5 | 7 | 4 | 8 | 7 | 7 | 9 | 9 | 9 | 8 | 6 | 9 | 8 | 8 | 8 | 9 | 9 |
| | | | | | | | | | 1 | 2 | | 7 | 6 | 7 | 8 | 9 | 8 | 7 | 5 | 9 | 7 | 6 | 8 | 9 | 8 |

TABLE XII-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 158 | 7 | 4 | 6 | 7 | 5 | 9 | 9 | 6 | 5 | 6 | 4 | 9 | 6 | 8 | 9 | 9 | 9 | 9 | 6 | 8 | 8 | 6 | 8 | 9 | 9 |
| | | | | | | | | | 1 | 5 | 2 | 8 | 5 | 4 | 9 | 8 | 7 | 8 | 5 | 8 | 7 | 5 | 8 | 8 | 8 |
| 159 | 6 | 5 | 6 | 7 | 2 | 6 | 7 | 5 | 5 | 6 | | 8 | 7 | 9 | 9 | 9 | 9 | 7 | 6 | 8 | 7 | 4 | 9 | 9 | 8 |
| | | | | | | | | | 1 | 5 | | 8 | 6 | 8 | 9 | 9 | 9 | 6 | 2 | 8 | 7 | 3 | 9 | 9 | 6 |
| 160 | 8 | | 6 | 6 | 4 | 6 | 8 | 8 | 5 | 7 | | 7 | 5 | 6 | 9 | 9 | 9 | 8 | 8 | 8 | 7 | 4 | 9 | 9 | 6 |
| | | | | | | | | | 1 | 6 | | 5 | 4 | 5 | 8 | 9 | 9 | 8 | 4 | 3 | 2 | 2 | 9 | 9 | 2 |
| 162 | 6 | 6 | 7 | 4 | 3 | 7 | 6 | 1 | 5 | 5 | | 7 | 5 | 7 | 9 | 8 | 7 | 4 | 1 | 7 | 4 | 2 | 9 | 9 | 4 |
| | | | | | | | | | 1 | 4 | | 2 | 2 | 7 | 9 | 8 | 6 | | | 6 | 2 | 1 | 9 | 8 | 2 |
| 163 | 2 | 2 | 5 | 2 | 4 | 5 | 6 | 2 | 5 | 6 | | 7 | 5 | 8 | 9 | 9 | 5 | 2 | | 5 | 2 | 4 | 9 | 9 | |
| | | | | | | | | | 1 | 2 | | 2 | 4 | 7 | 9 | 8 | 4 | | | 2 | 1 | 2 | 8 | 8 | |
| 164 | 7 | 6 | 7 | 4 | 6 | 7 | 6 | 5 | 5 | 6 | | 7 | 7 | 6 | 8 | 9 | 8 | 4 | | 7 | 6 | 5 | 9 | 9 | 5 |
| | | | | | | | | | 1 | 5 | | 6 | 3 | 5 | 7 | 9 | 7 | 2 | | 5 | 2 | 4 | 8 | 9 | |
| 165 | 5 | 4 | 6 | 5 | 3 | 7 | 7 | 6 | 5 | 6 | | 9 | 5 | 6 | 8 | 9 | 8 | 5 | 6 | 7 | 5 | 4 | 8 | 9 | |
| | | | | | | | | | 1 | 5 | | 4 | 2 | 4 | 8 | 9 | 6 | | 2 | | 2 | | 4 | 2 | |
| 166 | | | | | | | | | 5 | 4 | | 5 | 1 | 2 | 7 | 6 | 5 | 4 | | 5 | 1 | | 6 | 7 | |
| | | | | | | | | | 1 | 2 | | 2 | | | 5 | 2 | 2 | | | 2 | | | 2 | 5 | |
| 170 | | | 2 | | | 3 | 2 | 3 | 5 | 5 | | 6 | 5 | 6 | 9 | 8 | 7 | | | 3 | 2 | 3 | 8 | 9 | 2 |
| | | | | | | | | | 1 | 4 | | 5 | 3 | 5 | 8 | 7 | 6 | | | | | 1 | 6 | 8 | |
| 171 | 6 | | 4 | 3 | 5 | 8 | 7 | 6 | 5 | 3 | | 4 | 3 | 6 | 8 | 9 | 9 | 6 | | 2 | | 4 | 3 | 8 | 6 |
| | | | | | | | | | 1 | * | * | * | * | * | * | * | * | * | * | * | * | * | * | * | * |
| 172 | 7 | 6 | 6 | 7 | 3 | 8 | 8 | 6 | 5 | 4 | 3 | 6 | 4 | 6 | 9 | 9 | 9 | 4 | 5 | 6 | 5 | 3 | 9 | 9 | 5 |
| | | | | | | | | | 1 | 2 | | 5 | 3 | 5 | 9 | 9 | 8 | 3 | 4 | 4 | 5 | 3 | 9 | 8 | 4 |
| 173 | 3 | | 2 | 1 | 1 | 2 | 3 | | 5 | 4 | | 3 | 2 | 4 | 8 | 9 | 7 | | | | | | 4 | 3 | 2 |
| | | | | | | | | | 1 | 2 | | | | 3 | 8 | 8 | 6 | | | | | | 2 | 2 | |
| 174 | 2 | | 4 | 2 | 3 | 4 | 2 | 2 | 5 | 5 | 3 | 7 | 5 | 9 | 8 | 9 | 8 | 1 | | 2 | | 2 | 4 | 4 | 4 |
| | | | | | | | | | 1 | 4 | | 4 | 4 | 7 | 8 | 9 | 7 | | | | | | 2 | | 2 |
| 175 | 5 | | 2 | 2 | 4 | 5 | 4 | | 5 | 4 | 1 | 2 | 4 | 4 | 8 | 7 | 5 | | | | | | | | |
| | | | | | | | | | 1 | * | * | * | * | * | * | * | * | * | * | * | * | * | * | * | * |

We claim:

1. A compound of the formula I

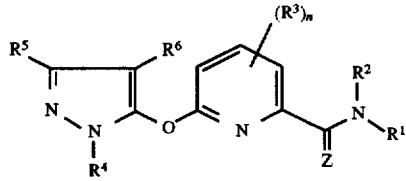

in which

Z represents an oxygen or sulphur atom, $R^1$ and $R^2$ each independently represents a hydrogen atom or an optionally substituted $C_{1-10}$alkyl, $C_{2-10}$alkenyl, $C_{2-10}$alkynyl, $C_{3-8}$cycloalkyl, $(C_{3-8}$cycloalkyl)$C_{1-10}$alkyl, $C_{6-10}$aryl, $C_{6-10}$aryl$C_{1-10}$alkyl or $C_{1-10}$alkyl$C_{6-10}$aryl group or one but not both of $R^1$ and $R^2$ may additionally represent a hydroxy group or an optionally substituted $C_{1-10}$alkoxy, $C_{2-10}$alkenyloxy, $C_{2-10}$alkynyloxy, $C_{1-10}$alkylcarbonyl, amino, mono- or di-$C_{1-10}$alkylamino, $C_{1-10}$alkoxycarbonylamino, $C_{6-10}$arylamino, $C_{6-10}$aryl$C_{1-10}$alkylamino or di$C_{1-10}$alkylcarbamoyl group, $R^3$ independently represents a halogen atom, a $C_{1-10}$alkyl, $C_{1-10}$alkoxy, $C_{1-10}$alkylthio, di$C_{1-10}$alkylamino or $C_{1-10}$haloalkyl group, $R^4$ represents a hydrogen or halogen atom, an optionally substituted $C_{1-10}$alkyl, $C_{2-10}$alkenyl, $C_{2-10}$alkynyl, $C_{3-8}$cycloalkyl, $(C_{3-8}$cycloalkyl) $C_{1-10}$alkyl, $C_{6-10}$aryl, $C_{6-10}$aryl$C_{1-10}$alkyl, $C_{1-10}$alkyl$C_{6-10}$aryl, $C_{1-10}$alkoxy, di$C_{1-10}$alkylcarbamoyl, acyl or a cyano group, $R^5$ and $R^6$ each independently represents a hydrogen or halogen atom, an optionally substituted $C_{1-10}$alkyl, $C_{2-10}$alkenyl, $C_{2-10}$alkynyl, $C_{3-8}$cycloalkyl, $(C_{3-8}$cycloalkyl)$C_{1-10}$alkyl, $C_{6-10}$aryl, $C_{6-10}$aryl$C_{1-10}$alkyl, $C_{1-10}$alkyl$C_{6-10}$aryl, $C_{1-10}$alkoxy, amino, mono-or di-$C_{1-10}$alkylamino, $C_{1-10}$alkoxycarbonylamino, $C_{6-10}$arylamino, di$C_{1-10}$alkylcarbamoyl group, and n represents 0, 1, 2 or 3, and in which said optional substituents are selected from the group consisting of halogen atoms or nitro, cyano, $C_{1-6}$ alkyl, $C_{1-6}$ haloalkyl, $C_{1-6}$ alkoxy, $C_{1-6}$ haloalkoxy, formyl, $C_{1-6}$ alkoxycarbonyl, carboxyl, phenyl or amino groups, said amino optionally substituted by one or two groups selected from $C_{1-10}$alkyl, $C_{6-10}$aryl, $C_{3-8}$cycloalkyl, $(C_{3-8}$cycloalkyl)$C_{1-10}$alkyl, $C_{6-10}$aryl$C_{1-10}$alkyl, and $C_{1-10}$alkyl$C_{6-10}$aryl.

2. A compound according to claim 1, in which Z represents an oxygen atom.

3. A compound according to claim 1 in which $R^1$ and $R^2$ each independently represents a hydrogen atom or a $C_{1-8}$ alkyl, $C_{2-8}$ alkenyl, $C_{2-8}$ alkynyl, $C_{3-6}$ cycloalkyl, $(C_{3-6}$ cycloalkyl) $C_{1-8}$ alkyl, $C_{1-6}$ alkoxy, phenyl, naphthyl, phen-$C_{1-6}$ alkyl, $C_{1-8}$ alkylamino, $C_{1-6}$ dialkylamino or phenylamino group, each group optionally substituted by one or more halogen atoms, $C_{1-4}$ alkyl, $C_{1-4}$ haloalkyl, $C_{1-4}$ alkoxy, $C_{1-4}$ alkylamino, $C_{1-4}$ dialkylamino, cyano or phenyl amino groups.

4. A compound according to claim 1 in which $R^3$ represents a methyl, methoxy, methylthio or dimethylamino group.

5. A compound according to claim 1 in which $R^4$, $R^5$ and $R^6$ each independently represents a hydrogen atom, a cyano group, a $C_{1-4}$ alkyl, $C_{3-6}$ cycloalkyl, $C_{1-4}$ acyl, $C_{2-4}$ alkenyl, phenyl or naphthyl group, each group optionally substituted by one, more halogen atoms or $C_{1-4}$ alkyl, $C_{1-4}$ haloalkyl, $C_{1-4}$ alkoxy, $C_{1-4}$ alkylamino, $C_{1-4}$ dialkylamino or $C_{6-10}$ aryl amino groups.

6. A herbicidal composition which comprises, as active ingredient, a compound as claimed in claim 1, together with at least one carrier.

7. The composition of claim 6 which comprises at least two carriers, at least one of which is a surface active agent.

8. A method of combating undesired plant growth at a locus, which comprises treating the locus with a compound as claimed in claim 1.

9. A method of combating undesired plant growth at a locus, which comprises treating the locus with a composition as claimed in claim 8.

10. A process for the preparation of a compound of the formula I as defined in claim 1, which comprises reacting a compound of the formula II,

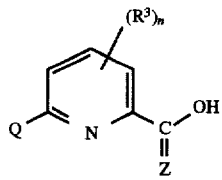

or an activated derivative thereof wherein the hydroxy group of the acid function is replaced by a leaving group selected from the group consisting of halogen, $C_{1-4}$ alkoxy and imidazole group, and in which $R^3$ and n are as defined in claim 1, and Q represents a leaving group selected from the group consisting of halogen, $C_{1-4}$ alkoxy, $C_{1-6}$ alkyl or aryl-sulphonium group, and $C_{1-6}$ alkyl or aryl-sulphonic acid group, with a compound of the formula III

HNR$^1$R$^2$     III in which the substituents are as defined in claim 1 and, followed by reaction of the product thus obtained with a compound of the formula

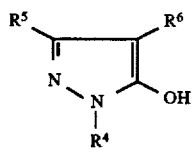

in which the substituents are defined in claim 1, while in the case that $R^1$ and/or $R^2$ represents a hydrogen atom, the hydrogen atom may be exchanged by another substituent within the definition of $R^1$ and/or $R^2$ by reaction with an alkylating agent.

* * * * *